US009155450B2

(12) United States Patent
Kawano

(10) Patent No.: US 9,155,450 B2
(45) Date of Patent: Oct. 13, 2015

(54) GUIDING APPARATUS AND CAPSULE MEDICAL DEVICE GUIDING SYSTEM

(71) Applicant: OLYMPUS MEDICAL SYSTEMS CORP., Tokyo (JP)

(72) Inventor: Hironao Kawano, Machida (JP)

(73) Assignee: OLYMPUS CORPORATION, Tokyo (JP)

(*) Notice: Subject to any disclaimer, the term of this patent is extended or adjusted under 35 U.S.C. 154(b) by 102 days.

(21) Appl. No.: 14/090,324

(22) Filed: Nov. 26, 2013

(65) Prior Publication Data
US 2014/0148643 A1    May 29, 2014

Related U.S. Application Data

(63) Continuation of application No. PCT/JP2013/062784, filed on May 2, 2013.

(30) Foreign Application Priority Data

May 7, 2012  (JP) .................................. 2012-106332

(51) Int. Cl.
*A61B 1/00* (2006.01)
*A61B 1/04* (2006.01)
(Continued)

(52) U.S. Cl.
CPC .......... *A61B 1/00158* (2013.01); *A61B 1/00006* (2013.01); *A61B 1/00055* (2013.01); *A61B 1/041* (2013.01); *A61B 5/704* (2013.01); *A61B 1/0002* (2013.01); *A61B 5/062* (2013.01)

(58) Field of Classification Search
CPC ............... A61B 1/041; A61B 1/00158; A61B 19/5244; A61B 2019/5246; A61B 2019/5251; A61B 2019/5253; A61B 5/06; A61B 5/061; A61B 5/062

USPC .................. 600/102, 109, 117, 118, 160, 178
See application file for complete search history.

(56) References Cited

U.S. PATENT DOCUMENTS

2005/0020911 A1   1/2005  Viswanathan et al.
2005/0093544 A1   5/2005  Ries
(Continued)

FOREIGN PATENT DOCUMENTS

DE           103 41 092 A1    4/2005
DE     10 2005 032 577 A1    1/2007
(Continued)

OTHER PUBLICATIONS

International Search Report dated Jun. 18, 2013 issued in PCT/JP2013/062784.
(Continued)

*Primary Examiner* — Anhtuan T Nguyen
*Assistant Examiner* — William Chou
(74) *Attorney, Agent, or Firm* — Scully, Scott, Murphy & Presser, PC

(57) ABSTRACT

A guiding apparatus includes a magnetic field generation unit, a translation mechanism that translates the magnetic field generation unit relative to a subject, a rotation mechanism that rotates the magnetic field generation unit relative to the subject, an input unit that receives first and second information about operations for changing a position a posture of a capsule medical device, respectively and a control unit that controls the translation mechanism and the rotation mechanism on the basis of the first information and the second information such that the magnetic field generation unit is translated and rotated relative to the subject, wherein, when the input unit receives the second information, the control unit corrects a change in the position of the capsule medical device caused by the rotation of the magnetic field generation unit relative to the subject by translating the magnetic field generation unit relative to the subject.

15 Claims, 20 Drawing Sheets

(51) Int. Cl.
*A61B 5/00* (2006.01)
*A61B 5/06* (2006.01)

(56) References Cited

U.S. PATENT DOCUMENTS

| | | |
|---|---|---|
| 2008/0300458 A1 | 12/2008 | Kim et al. |
| 2011/0184235 A1 | 7/2011 | Schostek et al. |
| 2011/0224490 A1 | 9/2011 | Kimura et al. |
| 2012/0095290 A1 | 4/2012 | Kawano |

FOREIGN PATENT DOCUMENTS

| | | |
|---|---|---|
| JP | 2007-044285 A | 2/2007 |
| JP | 2008-503310 A | 2/2008 |
| JP | 2011-147785 A | 8/2011 |
| WO | WO 2010/122823 A1 | 10/2010 |
| WO | WO 2011/118253 A1 | 9/2011 |

OTHER PUBLICATIONS

Extended Supplementary European Search Report dated Jun. 22, 2015 from related European Application No. 13 78 7588.6.

| TYPE | xyz | x-y-z | x-z-y | y-x-z | y-z-x | z-x-y | z-y-x |
|---|---|---|---|---|---|---|---|
| LENGTH IN x-AXIS DIRECTION | 100 | 200 | 200 | 100 | 50 | 100 | 50 |
| LENGTH IN y-AXIS DIRECTION | 100 | 100 | 50 | 200 | 200 | 50 | 100 |
| LENGTH IN z-AXIS DIRECTION | 100 | 50 | 100 | 50 | 100 | 200 | 200 |

| TYPE | xyz | y-x-z(75) | y-x-z(50) | y-x-z(33) |
|---|---|---|---|---|
| LENGTH IN x-AXIS DIRECTION | 100 | 100 | 100 | 100 |
| LENGTH IN y-AXIS DIRECTION | 100 | 133 | 200 | 300 |
| LENGTH IN z-AXIS DIRECTION | 100 | 75 | 50 | 33 |

GUIDING APPARATUS AND CAPSULE MEDICAL DEVICE GUIDING SYSTEM

CROSS REFERENCES TO RELATED APPLICATIONS

This application is a continuation of PCT international application Ser. No. PCT/JP2013/062784 filed on May 2, 2013 which designates the United States, incorporated herein by reference, and which claims the benefit of priority from Japanese Patent Applications No. 2012-106332, filed on May 7, 2012, incorporated herein by reference.

BACKGROUND OF THE INVENTION

1. Field of the Invention

The present invention relates to a guiding apparatus which guides a capsule medical device introduced into a subject and a capsule medical device guiding system.

2. Description of the Related Art

In the field of endoscopes, a capsule endoscope has been developed which is formed in a size capable of being introduced into the alimentary canal of the subject such as a patient. The capsule endoscope has an imaging function and a wireless communication function in a capsule-shaped casing. The capsule endoscope is swallowed through the mouth of the subject, sequentially acquires image data for the images (hereinafter, also referred to as in-vivo images) of the internal organs of the subject while being moved in the alimentary canal by a peristaltic motion, and wirelessly transmits the acquired image data to a receiving device outside the subject. The image data received by the receiving device is input to an image display device and the image display device performs predetermined image processing on the image data. In this way, the in-vivo image is displayed as a still image or a moving image on a display. The user, such as a doctor or a nurse, observes the in-vivo image displayed on the image display unit and diagnoses the state of the internal organs of the subject.

In recent years, a guiding system including a guiding apparatus which guides the capsule endoscope in the subject using magnetic force (hereinafter, referred to as magnetic guide) has been proposed (for example, see Japanese National Publication of International Patent Application No. 2008-503310). In general, in the guiding system, a permanent magnet (hereinafter, also referred to as an internal permanent magnet) is provided in the capsule endoscope. In addition, the guiding apparatus includes a magnetic field generation unit, such as an electromagnet or a permanent magnet (hereinafter, also referred to as an external permanent magnet), applies the magnetic field to the capsule endoscope introduced into the subject, and magnetically guides the capsule endoscope to a desired position using magnetic attraction generated from the applied magnetic field. In this case, the guiding system includes a display unit which receives the image data acquired by the capsule endoscope and can display the in-vivo image in real time. The user uses an operation input unit provided in the guiding system to perform an operation of magnetically guiding the capsule endoscope, while referring to the in-vivo image displayed on the display unit.

SUMMARY OF THE INVENTION

A guiding apparatus according to one aspect of the present invention is a guiding apparatus for guiding, in a subject, a capsule medical device introduced into the subject and including a permanent magnet by applying a magnetic field to the capsule medical device and includes: a magnetic field generation unit; a translation mechanism that translates the magnetic field generation unit relative to the subject; a rotation mechanism that rotates the magnetic field generation unit relative to the subject; an input unit that receives first information about an operation for changing a position of the capsule medical device and second information about an operation for changing a posture of the capsule medical device; and a control unit that controls the translation mechanism and the rotation mechanism in accordance with the first information and the second information such that the magnetic field generation unit is translated and rotated relative to the subject, wherein, when the input unit receives the second information, the control unit corrects a change in the position of the capsule medical device caused by the rotation of the magnetic field generation unit relative to the subject by translating the magnetic field generation unit relative to the subject.

A capsule medical device guiding system according to another aspect of the resent invention includes: a capsule medical device that includes a permanent magnet; and a guiding apparatus that applies a magnetic field to the capsule medical device introduced into a subject to guide the capsule medical device in the subject, wherein the guiding apparatus includes: a magnetic field generation unit; a translation mechanism that translates the magnetic field generation unit relative to the subject; a rotation mechanism that rotates the magnetic field generation unit relative to the subject; an input unit that receives first information about an operation for changing a position of the capsule medical device and second information about an operation for changing a posture of the capsule medical device; and a control unit that controls the translation mechanism and the rotation mechanism in accordance with the first information and the second information such that the magnetic field generation unit is translated and rotated relative to the subject, wherein, when the input unit receives the second information, the control unit corrects a change in the position of the capsule medical device caused by the rotation of the magnetic field generation unit relative to the subject by translating the magnetic field generation unit relative to the subject.

The above and other features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Figure 1:
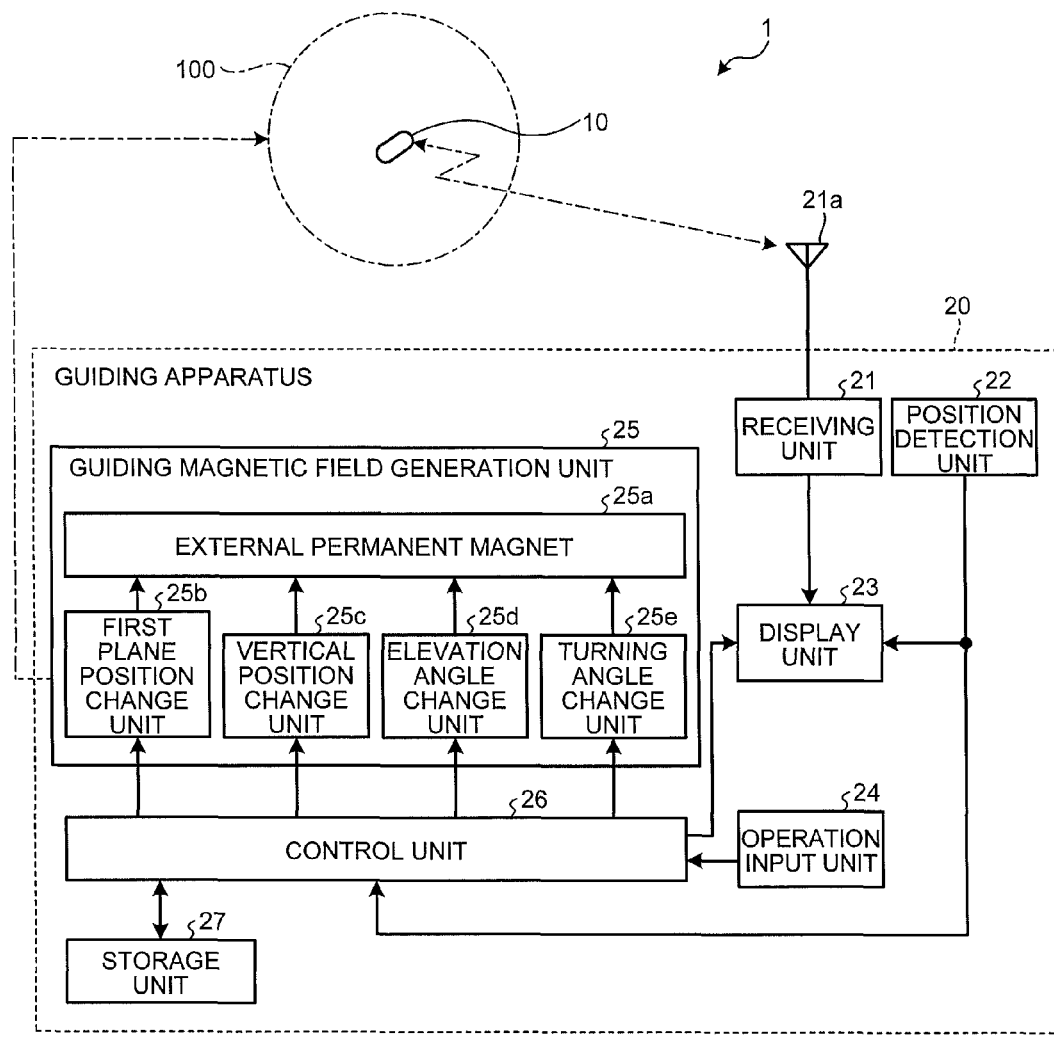
FIG. 1 is a diagram illustrating an example of the structure of a capsule medical device guiding system according to a first embodiment of the invention.

Hereinafter, a guiding apparatus and a capsule medical device guiding system according to embodiments of the invention will be described with reference to the drawings. In the following description, a capsule endoscope guiding system which uses, as a capsule medical device, a capsule endoscope that is introduced into the oral of a subject and floats in a liquid in the stomach of the subject is given as an example. However, the invention is not limited by the embodiment. That is, the invention may use various types of capsule medical devices, such as a capsule endoscope which is moved in the lumen from the gullet of the subject to the anus and a capsule endoscope which is introduced from the anus together with an isotonic solution. Further, in the following description, the drawings schematically illustrate a shape, a size, and a positional relationship such that the content of the invention can be easily understood. Therefore, the invention is not limited only to the shape, size, and positional relationship illustrated in the drawings. In the drawings, the same parts are denoted by the same reference numerals.

First Embodiment

Figure 2:
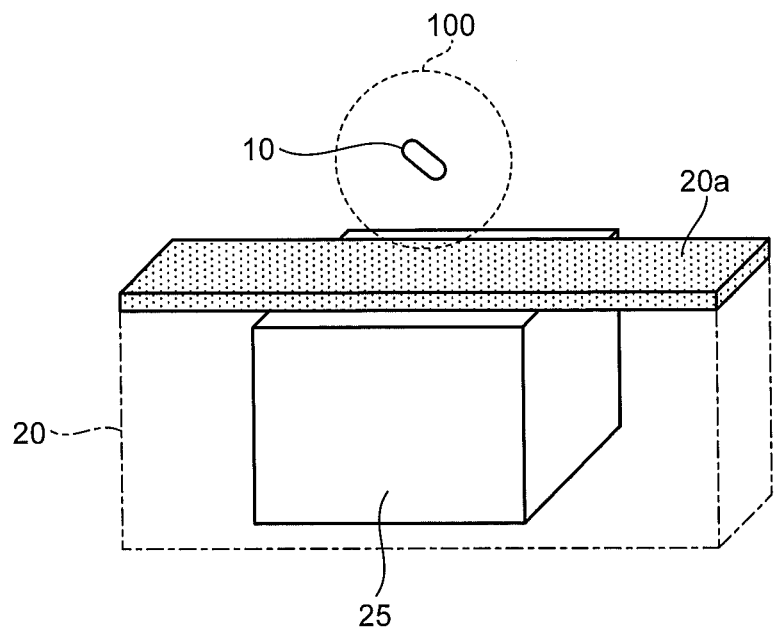
FIG. 2 is a schematic diagram illustrating an example of the outward appearance of a guiding apparatus illustrated in FIG. 1.

FIG. 1 is a schematic diagram illustrating an example of the structure of a capsule medical device guiding system according to a first embodiment of the invention. FIG. 2 is a schematic diagram illustrating an example of the outward appearance of a guiding apparatus illustrated in FIG. 1. As illustrated in FIG. 1, a capsule medical device guiding system 1 according to the first embodiment includes a capsule endoscope 10 which is a capsule medical device that is introduced into the body cavity of the subject and is provided with a permanent magnet and a guiding apparatus 20 that generates a three-dimensional magnetic field 100 to magnetically guide the capsule endoscope 10 introduced into the subject.

The capsule endoscope 10 is, for example, orally ingested together with a specific liquid, is introduced into the internal organs of the subject, is moved through the alimentary canal, and is finally excreted to the outside of the subject. The capsule endoscope 10 sequentially captures the in-vivo images of the subject while floating on the liquid introduced into the organs (for example, the stomach) of the subject and being magnetically guided by the magnetic field 100. Then, the capsule endoscope 10 sequentially wirelessly transmits image information (image data) corresponding to the captured in-vivo images. The detailed structure of the capsule endoscope 10 will be described.

The guiding apparatus 20 includes a receiving unit 21 that wirelessly communicates with the capsule endoscope 10 and receives a radio signal including the image information acquired by the capsule endoscope 10, a position detection unit 22 that detects the position of the capsule endoscope 10 in the subject in accordance with the radio signal received from the capsule endoscope 10, a display unit 23 that acquires image information from the radio signal received by the receiving unit 21, performs predetermined signal processing on the image information, displays the in-vivo image on a screen, and display the position of the capsule endoscope 10 in the subject on the screen, an operation input unit 24 that receives, for example, information for instructing various operations in the capsule medical device guiding system 1, a guiding magnetic field generation unit 25 that generates a magnetic field for guiding the capsule endoscope 10, a control unit 26 that controls these units, and a storage unit 27 that stores, for example, the image information captured by the capsule endoscope 10.

FIG. 2 is a perspective view schematically illustrating the outward appearance of the guiding apparatus 20. As illustrated in FIG. 2, the guiding apparatus 20 includes a bed 20a as a table on which the subject is placed. At least the guiding magnetic field generation unit 25 which generates the magnetic field 100 is arranged below the bed 20a.

The receiving unit 21 includes a plurality of antennas 21a and sequentially receives the radio signals from the capsule endoscope 10 through the plurality of antennas 21a. The receiving unit 21 selects an antenna with the highest receiving electric field intensity from the plurality of antennas 21a and performs, for example, a demodulation process on the radio signal which is received from the capsule endoscope 10 through the selected antenna. Then, the receiving unit 21 extracts image data related to the subject from the radio signal. The receiving unit 21 outputs an image signal included in the extracted image data to the display unit 23.

The position detection unit 22 performs an operation of estimating the position of the capsule endoscope 10 in the subject in accordance with the intensity of the radio signal received by the receiving unit 21.

The display unit 23 includes various types of displays, such as a liquid crystal display, generates a screen including the in-vivo image based on the image data input from the receiving unit 21 or other various kinds of information, and displays the screen on the display. Specifically, for example, the display unit 23 displays a group of the in-vivo images of the subject captured by the capsule endoscope 10 and displays information about the position or posture of the capsule endoscope 10 or information about a guiding operation. At that time, the display unit 23 may display the position or posture of the capsule endoscope 10 which is estimated from the magnetic field generated by the guiding apparatus 20 or it may display, on the screen, a position in the subject corresponding to the in-vivo image which is being display, in accordance with the detection result of the position by the position detection unit 22. In addition, the display unit 23 displays, for example, a reduced image of the in-vivo image which is selected under the control of the control unit 26 and the patient information and examination information of the subject.

The operation input unit 24 is implemented by an input device, such as a joystick, a console including various buttons and various switches, or a keyboard, and receives various kinds of information, such as guide instruction information for magnetically guiding the capsule endoscope 10 or setting information for setting a predetermined mode to the guiding apparatus 20. The guide instruction information is information for controlling the posture or position of the capsule endoscope 10 which is a magnetic guide operation target. Specifically, the guide instruction information includes information about an operation for changing the position of the capsule endoscope 10 or an operation for changing the inclination angle (angle with respect to the vertical axis) of the capsule endoscope 10 and information about an operation for changing the azimuth (angle about the vertical axis) of the view of the capsule endoscope 10 (imaging units 11A and 11B which will be described below). Hereinafter, the azimuth of the view is simply referred to as an azimuth. The operation input unit 24 inputs the received information to the control unit 26.

The guiding magnetic field generation unit 25 generates a magnetic field for changing the position, inclination angle, or azimuth of the capsule endoscope 10 introduced into the subject relative to the subject. Specifically, the guiding magnetic field generation unit 25 includes an external permanent magnet 25a serving as a magnetic field generation unit which generates the magnetic field, a first plane position change unit 25b serving as a mechanism which translates or rotates the external permanent magnet 25a, a vertical position change unit 25c, an elevation angle change unit 25d, and a turning angle change unit 25e.

Figure 3:
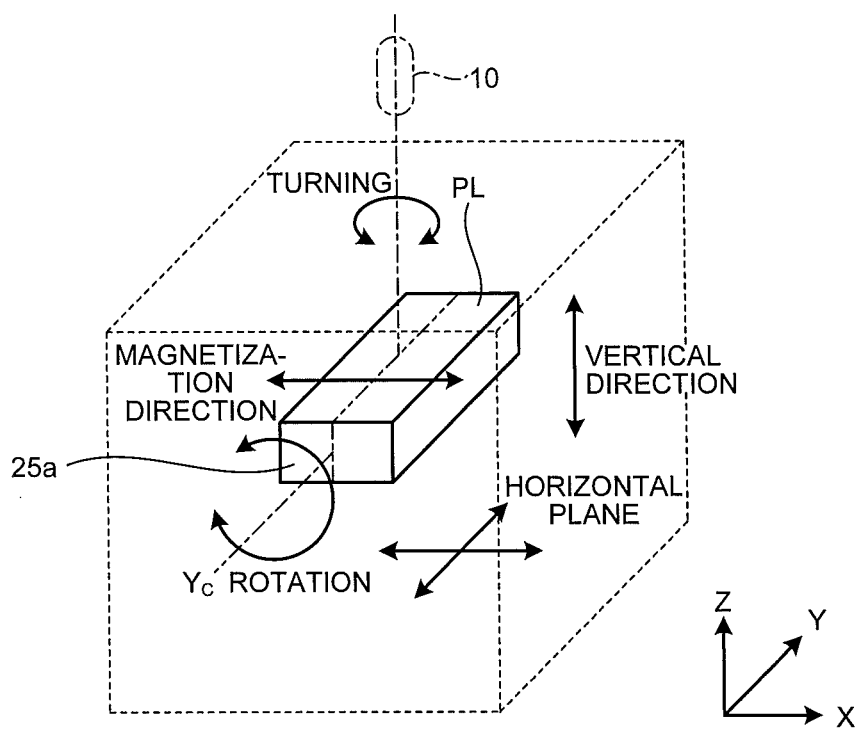
FIG. 3 is a schematic diagram illustrating the installation state of an external permanent magnet illustrated in FIG. 2.

FIG. 3 is a schematic diagram illustrating the arrangement state of the external permanent magnet 25a. As illustrated in FIG. 3, the external permanent magnet 25a is implemented by a bar magnet having, for example, a rectangular parallelepiped shape and restrains the movement of the capsule endoscope 10 in a region opposite to one plane (hereinafter, referred to as a capsule opposite plane PL) among four planes which are parallel to the magnetization direction.

The external permanent magnet 25a is arranged such that the capsule opposite plane PL is parallel to the horizontal plane in an initial state. Hereinafter, the arrangement of the external permanent magnet 25a when the external permanent magnet 25a is in the initial state is referred to as reference arrangement, the magnetization direction in the initial state is referred to as an X-axis direction, a direction in the horizontal plane perpendicular to the magnetization direction is referred to as a Y-axis direction, and the vertical direction is referred to as a Z-axis direction.

The external permanent magnet 25a has a shape in which, among the lengths of sides in three directions of the rectangular parallelepiped shape, the length of a size in the horizontal plane direction (in FIG. 3, the Y-axis direction) perpendicular to the magnetization direction is more than that in the magnetization direction (in FIG. 3, the X-axis direction) and the direction (in FIG. 3, the Z direction) perpendicular to the capsule opposite plane PL. Preferably, the external permanent magnet 25a has a flat plate shape in which, among the lengths of sides in three directions of the rectangular parallelepiped shape, the length in the direction perpendicular to the capsule opposite plane PL is the smallest. The shape of the external permanent magnet 25a will be described in detail below.

The first plane position change unit 25b is a translation mechanism which translates the external permanent magnet 25a in the horizontal plane. That is, the first plane position change unit 25b moves the external permanent magnet 25a in the horizontal plane while maintaining the relative position between two magnetic poles magnetized in the external permanent magnet 25a.

The vertical position change unit 25c is a translation mechanism which translates the external permanent magnet 25a in the vertical direction.

The elevation angle change unit 25d is a rotation mechanism which rotates the external permanent magnet 25a in the vertical plane including the permanent magnet to change an angle in the magnetization direction in the horizontal plane. Preferably, the elevation angle change unit 25d rotates the external permanent magnet 25a about an axis (hereinafter, referred to as a rotation axis $Y_C$) which is parallel to the capsule opposite plane PL, is perpendicular to the magnetization direction, and passes through the center of the external permanent magnet 25a. Hereinafter, the angle formed between the external permanent magnet 25a and the horizontal plane is referred to as an elevation angle θ.

The turning angle change unit 25e rotates the external permanent magnet 25a about a vertical axis which passes through the center of the external permanent magnet 25a. Hereinafter, the rotational motion of the external permanent magnet 25a about the vertical axis is referred to as a turning motion. In addition, the angle at which the external permanent magnet 25a turns with respect to the reference arrangement is referred to as a turning angle w.

The external permanent magnet 25a is turned at the turning angle ψ by the turning angle change unit 25e to change the angle of the rotation axis $Y_C$ with respect to the reference arrangement. In this state, the elevation angle change unit 25d rotates the external permanent magnet 25a about the rotation axis $Y_C$ to change the inclination angle and azimuth of the capsule endoscope 10 restrained by the magnetic field generated by the external permanent magnet 25a.

The control unit 26 controls the operation of each unit of the guiding magnetic field generation unit 25 in accordance with the detection result of the position detection unit 22 and the guide instruction information received by the operation input unit 24 to guide the capsule endoscope 10 to the position and posture desired by the user. At that time, the control unit 26 calculates a correction direction and the amount of correction in order to correct a change in the position of the capsule endoscope 10, which is not intended by the user, caused by the rotation of the external permanent magnet 25a and controls the operation of the first plane position change unit 25b in accordance with the calculated correction direction and amount of correction.

The storage unit 27 is implemented by a storage medium which can store information so as to be rewritable, such as a flash memory or a hard disk. The storage unit 27 stores information, such as various programs or various parameters which are used by the control unit 26 to control each unit of the guiding apparatus 20, in addition to image data for a group of the in-vivo images of the subject captured by the capsule endoscope 10.

Figure 4:
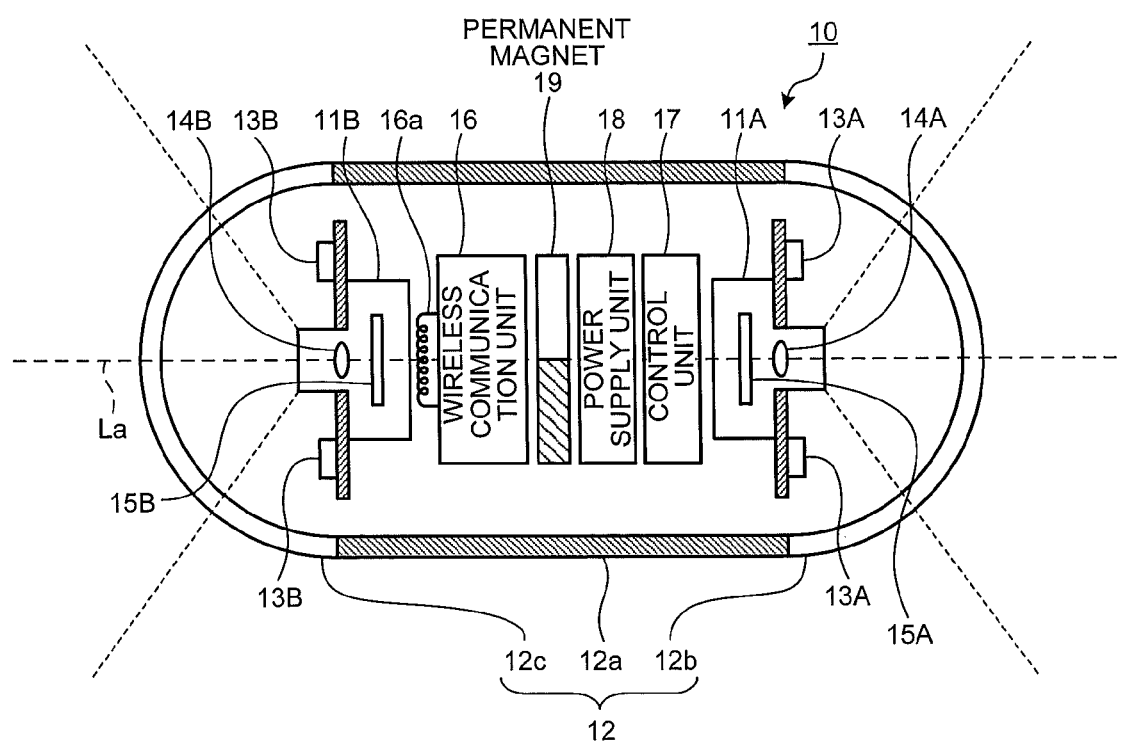
FIG. 4 is a schematic cross-sectional view illustrating an example of the internal structure of a capsule endoscope illustrated in FIG. 1.

Next, the detailed structure of the capsule endoscope 10 will be described. FIG. 4 is a schematic cross-sectional view illustrating an example of the internal structure of the capsule endoscope 10. As illustrated in FIG. 4, the capsule endoscope 10 includes a capsule-shaped casing 12 which is a case with a size that facilitates the introduction of the capsule endoscope 10 into the organs of the subject and imaging units 11A and 11B which captures the images of an object in different imaging directions and generate image information. In addition, the capsule endoscope 10 includes a wireless communication unit 16 which wirelessly transmits the image information generated by the imaging units 11A and 11B to the outside, a control unit 17 which controls each component of the capsule endoscope 10, and a power supply unit 18 which supplies power to each component of the capsule endoscope 10. The capsule endoscope 10 further includes a permanent magnet 19 for enabling the guiding apparatus 20 to perform magnetic guide.

The capsule-shaped casing 12 is an exterior case that is formed in a size which can be introduced into the internal organs of the subject and is implemented by covering both open ends of a cylindrical casing 12a with dome-shape casings 12b and 12c. The dome-shape casings 12b and 12c are dome-shaped optical members which are transparent with respect to light in a predetermined wavelength band, such as visible light. The cylindrical casing 12a is a colored casing which is substantially opaque with respect to visible light. As illustrated in FIG. 4, the capsule-shaped casing 12 formed by the cylindrical casing 12a and the dome-shape casings 12b and 12c liquid-tightly includes the imaging units 11A and 11B, the wireless communication unit 16, the control unit 17, the power supply unit 18, and the permanent magnet 19.

The imaging unit 11A includes an illumination unit 13A, such as an LED, an optical system 14A, such as a condenser lens, and an imaging element 15A, such as a CMOS image sensor or a CCD. The illumination unit 13A emits illumination light, such as white light, in the imaging field of view of the imaging element 15A and illuminates an object in the imaging field of view through the dome-shape casing 12b. The optical system 14A focuses light reflected from the imaging field of view on an imaging surface of the imaging element 15A and forms an object image in the imaging field of view. The imaging element 15A receives the light reflected from the imaging field of view which is focused on the imaging surface, performs a photoelectric conversion process for the received optical signal, and generates image information indicating the object image in the imaging field of view, that is, the in-vivo image of the subject.

Similarly to the imaging unit 11A, the imaging unit 11B includes an illumination unit 13B, such as an LED, an optical system 14B, such as a condenser lens, and an imaging element 15B, such as a CMOS image sensor or a CCD.

As illustrated in FIG. 4, when the capsule endoscope 10 is a binocular capsule medical device which captures the front and rear sides in the direction of a long axis La, the imaging units 11A and 11B are arranged such that the optical axes thereof are substantially parallel to or substantially aligned with the long axis La, which is the central axis of the capsule-shaped casing 12 in the longitudinal direction, and the imaging fields of view thereof are opposite to each other. That is, the imaging units 11A and 11B are mounted such that the imaging surfaces of the imaging elements 15A and 15B are perpendicular to the long axis La.

The wireless communication unit 16 includes an antenna 16a and sequentially wirelessly transmits the image information acquired by the imaging units 11A and 11B to the outside through the antenna 16a. Specifically, the wireless communication unit 16 acquires the image signal based on the image information which is generated by the imaging unit 11A or the imaging unit 11B from the control unit 17, modulates the image signal, and generates a radio signal. The wireless communication unit 16 transmits the radio signal to an external receiving unit 21 through the antenna 16a.

The control unit 17 controls the operations of the imaging units 11A and 11B and the wireless communication unit 16 and controls the input and output of signals between the components. Specifically, the control unit 17 directs the imaging element 15A to capture the image of the object in the imaging field of view illuminated by the illumination unit 13A and directs the imaging element 15B to capture the image of the object in the imaging field of view illuminated by the illumination unit 13B. In addition, the control unit 17 has a signal processing function for generating an image signal. Whenever acquiring image information from the imaging elements 15A and 15B, the control unit 17 performs predetermined signal processing for the image information and generates an image signal including image data. Furthermore, the control unit 17 controls the wireless communication unit 16 such that the image signals are sequentially wirelessly transmitted in time series to the outside.

The power supply unit 18 is an electric storage unit, such as a button-shaped battery or a capacitor, and includes a switching unit, such as a magnetic switch or an optical switch. The power supply unit 18 switches the on and off states of power in response to the magnetic field which is applied from the outside. In the on state, the power supply unit 18 appropriately supplies power from the electric storage unit to each component (the imaging units 11A and 11B, the wireless communication unit 16, and the control unit 17) of the capsule endoscope 10. In the off state, the power supply unit 18 stops the supply of power to each component of the capsule endoscope 10.

The permanent magnet 19 enables the magnetic guide of the capsule endoscope 10 by the magnetic field 100 generated by the guiding magnetic field generation unit 25 and is fixed in the capsule-shaped casing 12 such that the magnetization direction is inclined with respect to the long axis La. Specifically, the permanent magnet 19 is arranged such that the magnetization direction is perpendicular to the long axis La. The permanent magnet 19 operates so as to follow the magnetic field applied from the outside. As a result, the capsule endoscope 10 is magnetically guided by the guiding magnetic field generation unit 25.

Figure 5:
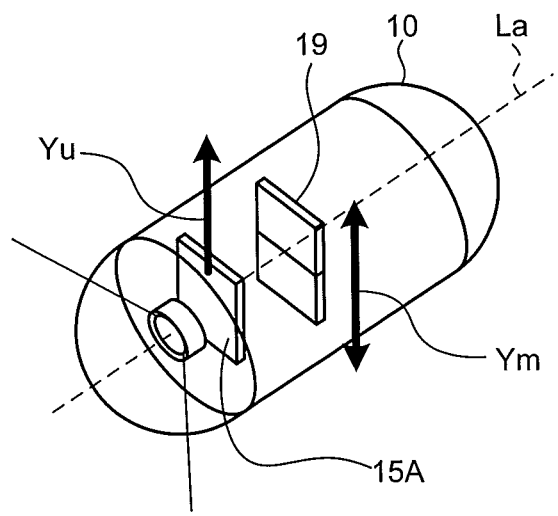
FIG. 5 is a schematic diagram illustrating the relative positional relationship between an imaging element and a permanent magnet in the capsule endoscope.

Next, the relative positional relationship between the imaging elements 15A and 15B and the permanent magnet 19 will be described with reference to FIG. 5. The permanent magnet 19 is arranged in the capsule-shaped casing 12 so as to be fixed relative to the imaging units 11A and 11B. Specifically, the permanent magnet 19 is arranged such that the magnetization direction is fixed relative to the up-down direction of each of the imaging surfaces of the imaging elements 15A and 15B. Specifically, as illustrated in FIG. 5, the permanent magnet 19 is arranged such that a magnetization direction Ym is parallel to the up-down direction Yu of each of the imaging surfaces of the imaging elements 15A and 15B.

Figure 6:
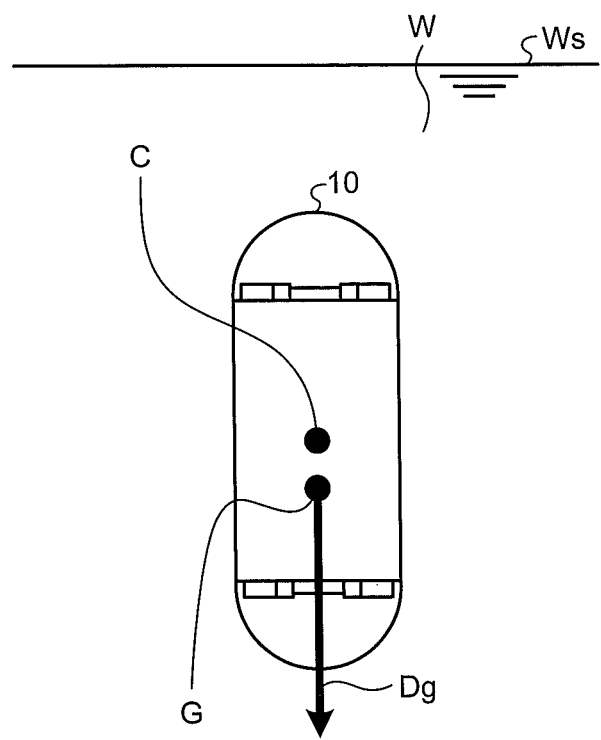
FIG. 6 is a conceptual diagram illustrating an aspect of the capsule endoscope (a state in which no magnetic field is applied) in a state in which a liquid is introduced into the subject.

FIG. 6 is a conceptual diagram illustrating an aspect of the capsule endoscope 10 with a liquid W being introduced into the subject. FIG. 6 illustrates a state in which the magnetic field generated by the guiding magnetic field generation unit 25 for controlling the position and posture of the capsule endoscope 10 is not applied to the permanent magnet 19 of the capsule endoscope 10.

The capsule endoscope 10 according to the first embodiment is designed so as to float in the liquid W. The center of gravity G of the capsule endoscope 10 is set so as to deviate from the geometric center C of the capsule endoscope 10 along the long axis La of the capsule endoscope 10 (the central axis of the capsule endoscope 10 in the longitudinal direction: see FIG. 4). Specifically, the arrangement of each component, such as the power supply unit 18 and the permanent magnet 19, is adjusted to set the center of gravity G of the capsule endoscope 10 at a position that is on the long axis La and is away from the geometric center C of the capsule-shaped casing 12 to the imaging unit 11B. Therefore, the capsule endoscope 10 floats in the liquid W, with the long axis La being substantially parallel to the vertical direction (that is, the gravity direction). In other words, the capsule endoscope 10 floats in the liquid W, with a line connecting the geometric center C and the center of gravity G being aligned with the vertical direction. When the capsule endoscope 10 is at the upright position, the imaging field of view of the imaging unit 11A faces upward in the vertical direction, and the imaging field of view of the imaging unit 11B faces downward in the vertical direction. The liquid W is a liquid that is harmless to the human body, such as water or a saline solution.

As described above, the permanent magnet 19 is arranged such that the magnetization direction Ym (see FIG. 5) is perpendicular to the long axis La. That is, the magnetization direction Ym of the permanent magnet 19 is aligned with the diametrical direction of the capsule endoscope 10. Therefore, when the magnetic field for controlling the position and posture of the capsule endoscope 10 is not applied to the permanent magnet 19, the capsule endoscope 10 floats in the liquid W with the magnetization direction Ym being aligned with the horizontal direction. In this case, a plane including the magnetization direction Ym and a line which connects the geometric center C and the center of gravity G of the capsule-shaped casing 12 is the vertical plane.

Figure 7:
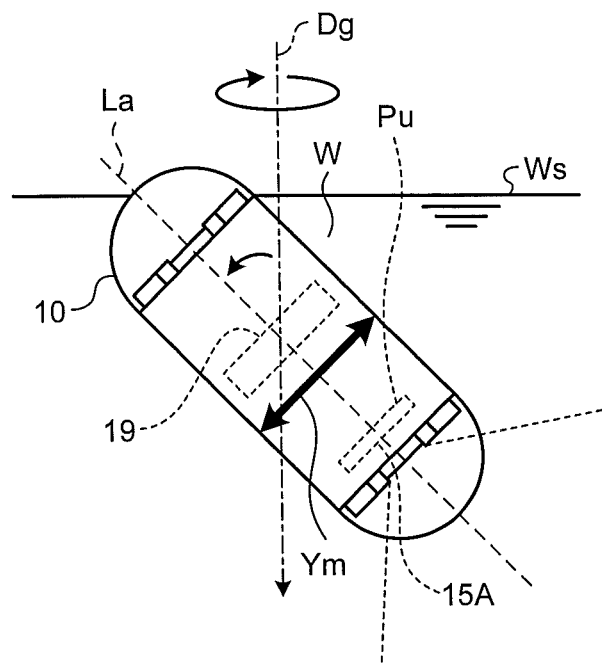
FIG. 7 is a conceptual diagram illustrating an aspect of the capsule endoscope (a state in which a magnetic field is applied) in a state in which a liquid is introduced into the subject.

FIG. 7 is a conceptual diagram illustrating an aspect of the capsule endoscope 10, with the liquid W being introduced into the subject, and illustrates a state in which the magnetic field for controlling the inclination angle of the capsule endoscope 10 is applied to the permanent magnet 19.

As illustrated in FIG. 7, the inclination of the long axis La of the capsule endoscope 10 with respect to a gravity direction Dg can be controlled such that the magnetic field from the outside is applied to the permanent magnet 19 of the capsule endoscope 10. For example, the magnetic field in which the direction of magnetic field lines is inclined with respect to the horizontal plane is applied to the permanent magnet 19 to incline the capsule endoscope 10 with respect to the gravity direction Dg such that the magnetization direction Ym of the permanent magnet 19 is substantially parallel to the magnetic field line. In this case, the posture of the capsule endoscope 10 is changed while the magnetization direction Ym is being included in the vertical plane. The elevation angle change unit 25d of the guiding apparatus 20 changes the elevation angle θ of the external permanent magnet 25a to obtain the magnetic field for the above-mentioned control operation (see FIGS. 1 and 3).

With the capsule endoscope 10 being inclined, the magnetic field which is turned about the gravity direction Dg is applied to turn the capsule endoscope 10 about the gravity direction Dg, as represented by an arrow. In this way, it is possible to easily acquire an in-vivo image around the capsule endoscope 10. The turning angle change unit 25e of the guiding apparatus 20 turns the external permanent magnet 25a to obtain the magnetic field for the above-mentioned control operation (see FIGS. 1 and 3).

Figure 8:
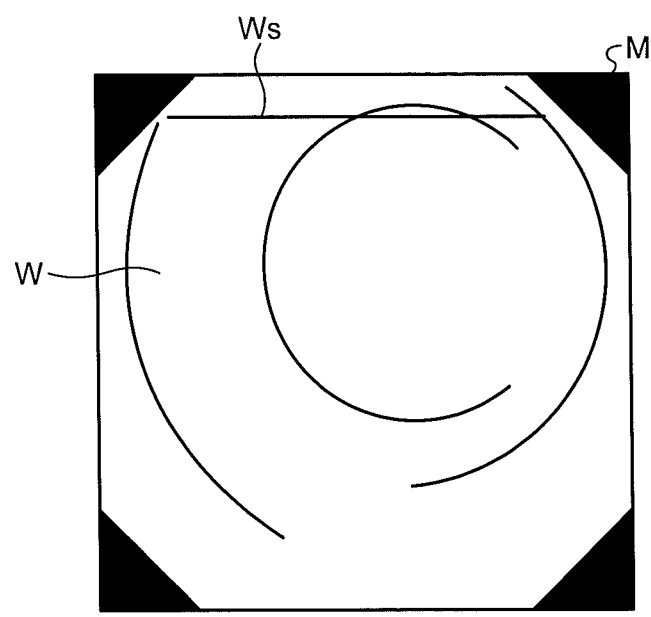
FIG. 8 is a diagram illustrating an example of an image which is displayed on a display screen of a display unit illustrated in FIG. 1.

In this case, the display unit 23 of the guiding apparatus 20 displays the in-vivo image of the subject captured by the capsule endoscope 10 such that the up-down direction of the object in the in-vivo image is aligned with the up-down direction of the display screen, with the magnetic guide of the capsule endoscope 10. As a result, as illustrated in FIG. 8, a liquid level Ws which is captured by an element in an upper region Pu of the imaging element 15A of the capsule endoscope 10 is displayed on a display screen M of the display unit 23 so as to be arranged in an upper part of the image corresponding to the imaging unit 11A. Since the magnetization direction Ym of the permanent magnet 19 is parallel to the up-down direction Yu of each of the imaging surfaces of the imaging elements 15A and 15B, a direction parallel to the magnetization direction Ym of the permanent magnet 19 is aligned with the up-down direction of the display screen of the display unit 23.

Figure 9A:
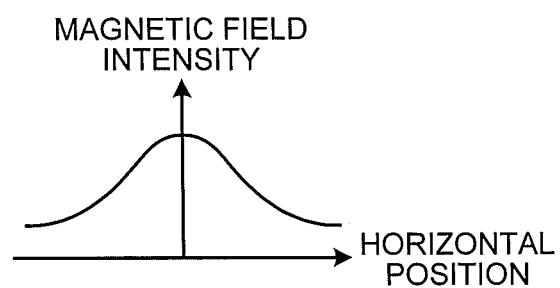
FIGS. 9A and 9B are schematic diagrams illustrating a method of controlling the position of the capsule endoscope in the vertical direction.
Figure 9B:
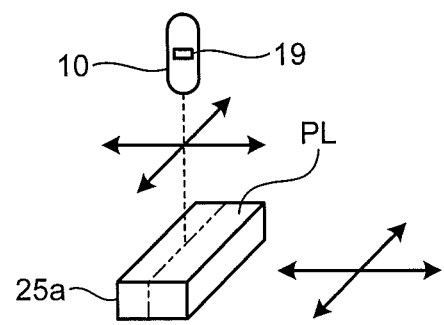

As illustrated in FIGS. 9A and 9B, the translational motion of the capsule endoscope 10 in the horizontal direction can be controlled by applying the magnetic field (see FIG. 9A) having the peak of magnetic field intensity in the capsule opposite plane PL to the permanent magnet 19 of the capsule endoscope 10 to attract the permanent magnet 19 to the peak position of the magnetic field, thereby restraining the movement of the capsule endoscope 10 (see FIG. 9B). Specifically, the first plane position change unit 25b of the guiding apparatus 20 moves the external permanent magnet 25a in the horizontal plane to obtain the magnetic field.

Figure 10A:
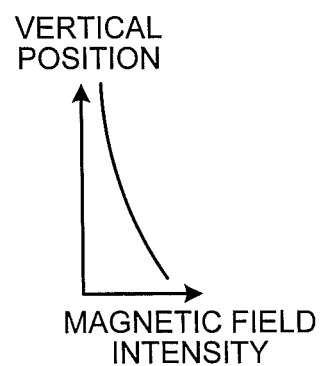
FIGS. 10A and 10B are schematic diagrams illustrating a method of controlling the position of the capsule endoscope in the horizontal direction.
Figure 10B:
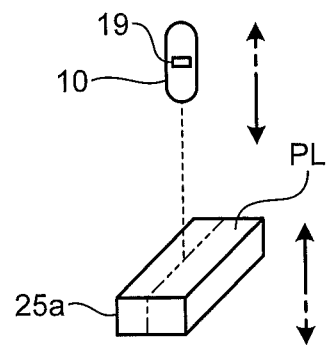

As illustrated in FIGS. 10A and 10B, the translational motion of the capsule endoscope 10 in the vertical direction can be controlled by applying the magnetic field whose magnetic field gradient distribution varies depending on the distance in the direction perpendicular to the capsule opposite plane PL to the permanent magnet 19 of the capsule endoscope 10. Specifically, the vertical position change unit 25c of the guiding apparatus 20 moves the external permanent magnet 25a in the vertical direction to obtain the magnetic field.

For example, as illustrated in FIG. 10A, when the capsule opposite plane PL is horizontal, the magnetic field whose magnetic field gradient is reduced as the height of the vertical position increases is applied to the permanent magnet 19. In this case, as illustrated in FIG. 10B, when the external permanent magnet 25a is moved up and down to relatively lower the vertical position of the permanent magnet 19, the magnetic attraction applied to the permanent magnet 19 is strengthened and the capsule endoscope 10 is urged downward. The position of the capsule endoscope 10 in the vertical direction is substantially maintained by the balance among the buoyancy of the capsule endoscope 10 with respect to the liquid W, gravity applied to the capsule endoscope 10, and magnetic attraction applied by the external permanent magnet 25a.

Next, the detailed structure and operation of the operation input unit 24 illustrated in FIG. 1 will be described.

Figure 11A:
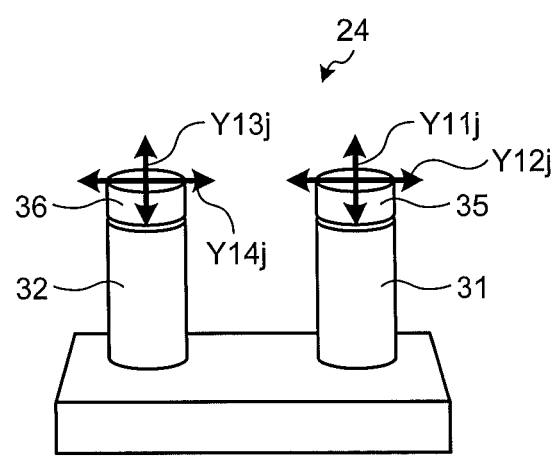
FIGS. 11A and 11B are diagrams illustrating an example of an operation input unit illustrated in FIG. 1.
Figure 11B:
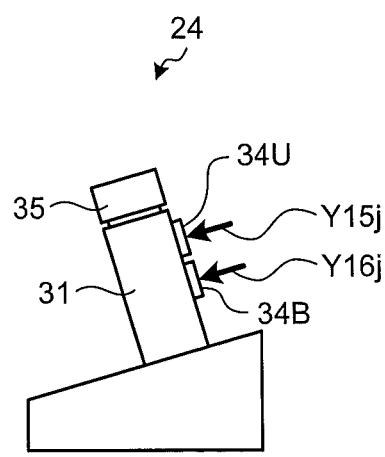
Figure 12:
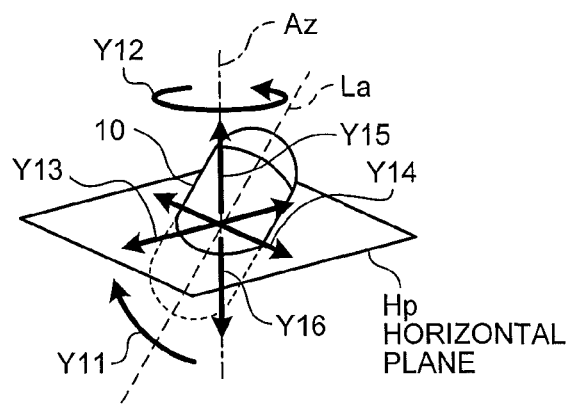
FIG. 12 is a diagram illustrating the magnetic guide of the capsule medical device which can be operated by the operation input unit illustrated in FIG. 1.

FIG. 11A is a front view illustrating the operation input unit 24 and FIG. 11B is a right side view illustrating the operation input unit 24. FIG. 12 is a diagram illustrating the movement of the capsule endoscope 10 designated by the operation of each component of the operation input unit 24.

As illustrated in FIG. 11A, the operation input unit 24 includes two joysticks 31 and 32 for three-dimensionally operating the magnetic guide of the capsule endoscope 10 by the guiding magnetic field generation unit 25. The joysticks 31 and 32 can be tilted in the up-down direction and the left-right direction.

As illustrated in FIG. 11B, an up button 34U and a down button 34B are provided on the rear surface of the joystick 31. The up button 34U is pressed to input guide instruction information for instructing the upward guide of the capsule endoscope 10 to the control unit 26 and the down button 34B is pressed to input guide instruction information for instructing the downward guide of the capsule endoscope 10 to the control unit 26. A capture button 35 is provided in an upper part of the joystick 31. The capture button 35 is pressed to capture the in-vivo image displayed on the display unit 23. In addition, an approach button 36 is provided in an upper part of the joystick 32. The approach button 36 is pressed to input, to the control unit 26, guide instruction information for guiding the capsule endoscope 10 such that the imaging unit 11A of the capsule endoscope 10 approaches the target to be captured by the imaging unit 11A.

As illustrated in FIG. 11A, the up/down tilt direction of the joystick 31 represented by an arrow Y11j corresponds to a tilting guide direction in which the head of the capsule endoscope 10 is shaken such that the leading end of the capsule endoscope 10 passes through the vertical axis Az, as represented by an arrow Y11 in FIG. 12. When the operation input unit 24 inputs guide instruction information corresponding to the tilt operation of the joystick 31 represented by the arrow Y11j to the control unit 26, the control unit 26 calculates the guide direction of the leading end of the capsule endoscope 10 in the absolute coordinate system according to the tilt direction of the joystick 31 and calculates the amount of guide according to the tilt operation of the joystick 31, in accordance with the guide instruction information. Then, for example, the guiding magnetic field generation unit 25 controls the elevation angle change unit 25d such that the elevation angle θ of the external permanent magnet 25a is changed in the calculated guide direction in accordance with the calculated amount of guide.

As illustrated in FIG. 11A, the left-right tilt direction of the joystick 31 represented by an arrow Y12j corresponds to a rotation guide direction in which the capsule endoscope 10 is rotated about the vertical axis Az, as represented by an arrow Y12 in FIG. 12. When the operation input unit 24 inputs guide instruction information corresponding to the tilt operation of the joystick 31 represented by the arrow Y12j to the control unit 26, the control unit 26 calculates the guide direction of the leading end of the capsule endoscope 10 in the absolute coordinate system according to the tilt direction of the joystick 31 and calculates the amount of guide according to the tilt operation of the joystick 31, in accordance with the guide instruction information. In addition, for example, the control unit 26 controls the turning angle change unit 25e such that the external permanent magnet 25a is turned in the calculated guide direction in accordance with the calculated amount of guide.

As illustrated in FIG. 11A, the up-down tilt direction of the joystick 32 represented by an arrow Y13j corresponds to a horizontal backward guide direction or a horizontal forward guide direction in which the long axis La of the capsule endoscope 10 is projected to a horizontal plane Hp and the capsule endoscope 10 is moved, as represented by an arrow Y13 in FIG. 12. When the operation input unit 24 inputs guide instruction information corresponding to the tilt operation of the joystick 32 represented by the arrow Y13j to the control unit 26, the control unit 26 calculates the guide direction and the amount of guide of the leading end of the capsule endoscope 10 in the absolute coordinate system according to the tilt direction of the joystick 32, in accordance with the guide instruction information, and controls the first plane position change unit 25b such that the external permanent magnet 25a is translated in accordance with the calculated guide direction and amount of guide.

As illustrated in FIG. 11A, the left-right tilt direction of the joystick 32 represented by an arrow Y14j corresponds to a horizontal right guide direction or a horizontal left guide direction which is perpendicular to the projection direction of the long axis La of the capsule endoscope 10 to horizontal plane Hp and in which the capsule endoscope 10 is moved, as represented by an arrow Y14 in FIG. 12. When the operation input unit 24 inputs guide instruction information corresponding to the tilt operation of the joystick 32 represented by the arrow Y14j to the control unit 26, the control unit 26 calculates the guide direction and the amount of guide of the leading end of the capsule endoscope 10 in the absolute coordinate system according to the tilt direction of the joystick 32, in accordance with the guide instruction information, and controls the first plane position change unit 25b such that the external permanent magnet 25a is translated in accordance with the calculated guide direction and amount of guide.

The up button 34U and the down button 34B are provided on the rear surface of the joystick 32. When the up button 34U is pressed as represented by an arrow Y15j in FIG. 11B, an up operation of moving up the capsule endoscope 10 along the vertical axis Az illustrated in FIG. 12 is instructed, as represented by an arrow Y15. When the down button 34B is pressed as represented by an arrow Y16j in FIG. 11B, a down operation of moving down the capsule endoscope 10 along the vertical axis Az illustrated in FIG. 12 is instructed, as represented by an arrow Y16. When the operation input unit 24 inputs guide instruction information corresponding to the press operation of the up button 34U or the down button 34B represented by the arrow Y15j or Y16j to the control unit 26, the control unit 26 calculates the guide direction and the amount of guide of the leading end of the capsule endoscope 10 in the absolute coordinate system according to the pressed button, in accordance with the guide instruction information, and controls the vertical position change unit 25c such that the external permanent magnet 25a is translated in the vertical direction in accordance with the calculated guide direction and amount of guide. For example, when the up button 34U is pressed, the vertical position change unit 25c translates the external permanent magnet 25a in the downward direction (a direction in which the external permanent magnet 25a is separated from the capsule endoscope 10) along the vertical axis Az. Then, the capsule endoscope 10 rises, as represented by the arrow Y15. When the down button 34B is pressed, the vertical position change unit 25c translates the external permanent magnet 25a in the upward direction (a direction in which the external permanent magnet 25a approaches the capsule endoscope 10) along the vertical axis Az. Then, the capsule endoscope 10 falls, as represented by the arrow Y16.

The operation input unit 24 may further include an input device including various operation buttons or a keyboard, in addition to the joysticks 31 and 32.

Figure 13:
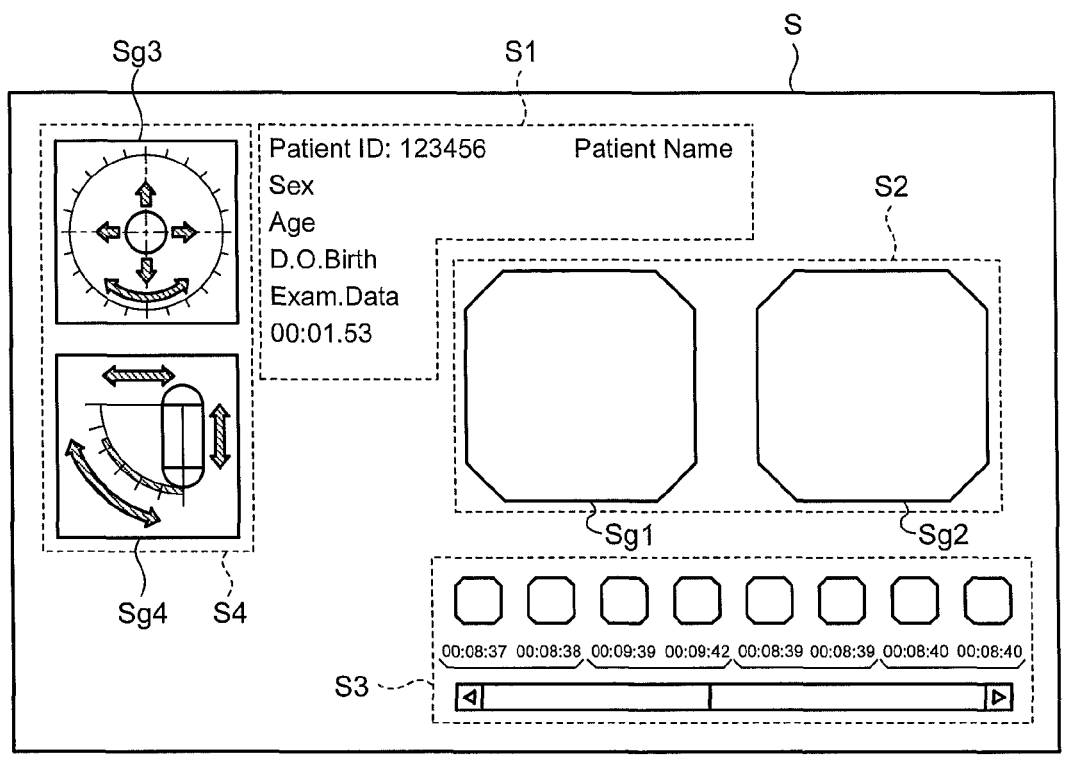
FIG. 13 is a diagram illustrating an example of a menu screen displayed on the display unit.

FIG. 13 is a schematic diagram illustrating an example of the display of a menu screen S on the display unit 23. In the menu screen S, information about each subject, such as the patient name, patient ID, birth date, sex, and age of the subject, is displayed in an upper left area S1, an in-vivo image Sg1 captured by the imaging unit 11A is displayed on the left side of a central area S2, an in-vivo image Sg2 captured by the imaging unit 11B is displayed on the right side of the central area S2, each image captured by the capture operation of the capture button 35 is reduced and displayed in an area S3 below the area S2 together with a capture time, and a posture diagram Sg3 in the vertical plane and a posture diagram Sg4 in the horizontal plane are displayed as posture diagrams of the capsule endoscope 10 in a left area S4. The postures of the capsule endoscope 10 displayed on the posture diagrams Sg3 and Sg4 indicate postures corresponding to the guide instruction information of the operation input unit 24. In the first embodiment, since the amount of input from the operation input unit 24 is reflected in guiding force, it can be considered that the displayed posture of the capsule endoscope 10 is substantially the same as the actual posture of the capsule endoscope 10 and guide instruction assistance for the operator is improved. In the posture diagrams Sg3 and Sg4, the direction in which the capsule endoscope 10 can be guided is represented by an arrow. When an operation of designating the guide direction operation is input, the display color of the arrow corresponding to the input direction is changed to support the operation of the operator.

Next, the operation of the control unit 26 when the posture of the capsule endoscope 10 is changed will be described. When the external permanent magnet 25a is rotated to change the posture of the capsule endoscope 10, a driving force for moving the capsule endoscope 10 in the horizontal plane is generated by a change in the magnetic field due to the rotation of the external permanent magnet 25a and the restraint position of the capsule endoscope 10 deviates from the position which is intended by the user.

Figure 14:
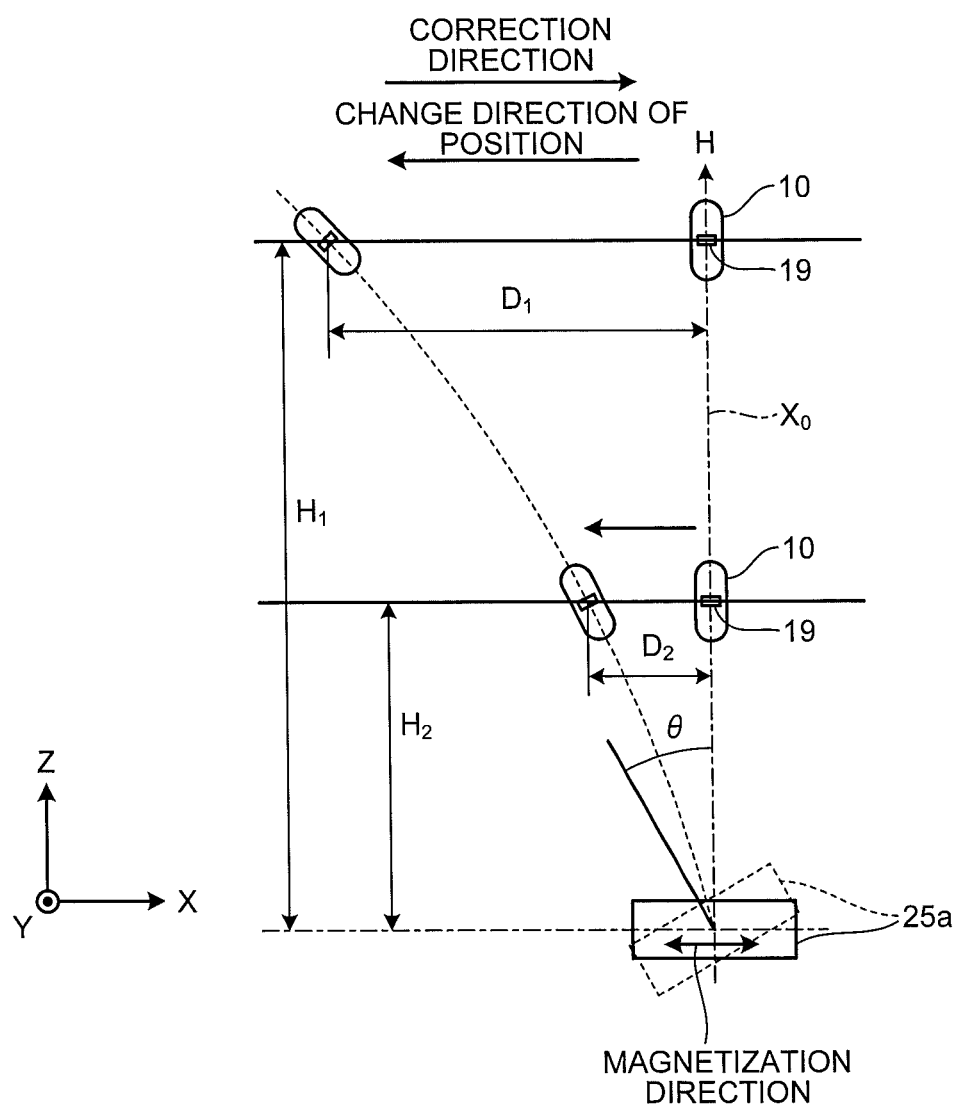
FIG. 14 is a conceptual diagram illustrating the principle of correcting the restraint position of the capsule endoscope.

For example, as illustrated in FIG. 14, the restraint position of the capsule endoscope 10 in the vertical plane (ZX plane) is determined by the distance between the capsule endoscope 10 and the external permanent magnet 25a in the vertical direction, that is, the height H of the capsule endoscope 10 and the turning angle θ of the external permanent magnet 25a. Therefore, when the capsule endoscope 10 is disposed at $X=X_0$ and $Z=H_n$ (n=1, 2, . . . ) and the external permanent magnet 25a is rotated by an elevation angle $\theta_n$, the restraint position of the capsule endoscope 10 is changed by a distance $D_n$ in the −X-axis direction.

Therefore, in order to maintain the capsule endoscope 10 at the original position ($X=X_0$), the control unit 26 performs control such that the capsule endoscope 10 is moved by a distance (correction amount) corresponding to the amount of change generated by the rotation of the external permanent magnet 25a in a direction (correction direction) opposite to the direction in which the position of the capsule endoscope 10 is changed. In this way, a change in the restraint position of the capsule endoscope 10 is offset.

In the actual XYZ coordinate system, the correction direction is opposite to the rotation direction of the external permanent magnet 25a by the elevation angle change unit 25d about an intersecting axis between the vertical plane and the horizontal plane including the magnetization direction of the external permanent magnet 25a. The correction amount $D_n$ is divided into a correction amount in the X-axis direction and a correction amount in the Y-axis direction in accordance with the turning angle ψ of the external permanent magnet 25a which gives the azimuth of the capsule endoscope 10.

As a specific operation, the control unit 26 acquires the position (corresponding to distances $H_1$ and $H_2$ illustrated in FIG. 14) of the capsule endoscope 10 in the vertical direction from the detection result output from the position detection unit 22. In addition, the control unit 26 calculates the turning angle ψ, elevation angle θ, translation direction, and translation amount of the external permanent magnet 25a required to change the azimuth and inclination angle of the capsule endoscope 10 which are desired by the user and to move the capsule endoscope 10 from the guide instruction information input from the operation input unit 24. Then, in order to correct a change in the restraint position of the capsule endoscope 10 caused by the rotation of the external permanent magnet 25a, the control unit 26 calculates the correction direction using the turning angle ψ and calculates the correction amount using the elevation angle θ. A calculation formula used in this case is stored in the storage unit 27 in advance. The control unit 26 corrects the translation direction and translation amount of the external permanent magnet 25a based on the guide instruction information, using the calculated correction direction and correction amount. Then, the control unit 26 turns and rotates the external permanent magnet 25a at the calculated turning angle ψ and elevation angle θ and controls each unit of the guiding magnetic field generation unit 25 such that the external permanent magnet 25a is translated in the corrected translation direction with the corrected translation amount.

Instead of calculating the correction direction and the correction amount, the control unit 26 may store the correction direction and the correction amount which are associated with the turning angle ψ and elevation angle θ of the external permanent magnet 25a and the position of the capsule endoscope 10 in the vertical direction in the storage unit 27 in advance and may extract a necessary correction direction and a necessary correction amount from the storage unit 27 in accordance with the input guide instruction information and the detection result of the position detection unit 22 (the position of the capsule endoscope 10 in the vertical direction) when the operation input unit 24 inputs guide instruction information for rotating the capsule endoscope 10.

In addition, when the first plane position change unit 25b translates the external permanent magnet 25a, the control unit 26 may adjust the translational velocity of the external permanent magnet 25a in accordance with the translation amount such that the movement of the capsule endoscope 10 is completed within a predetermined period of time.

Next, conditions for the shape of the external permanent magnet 25a will be described.

Figures 15, 16:
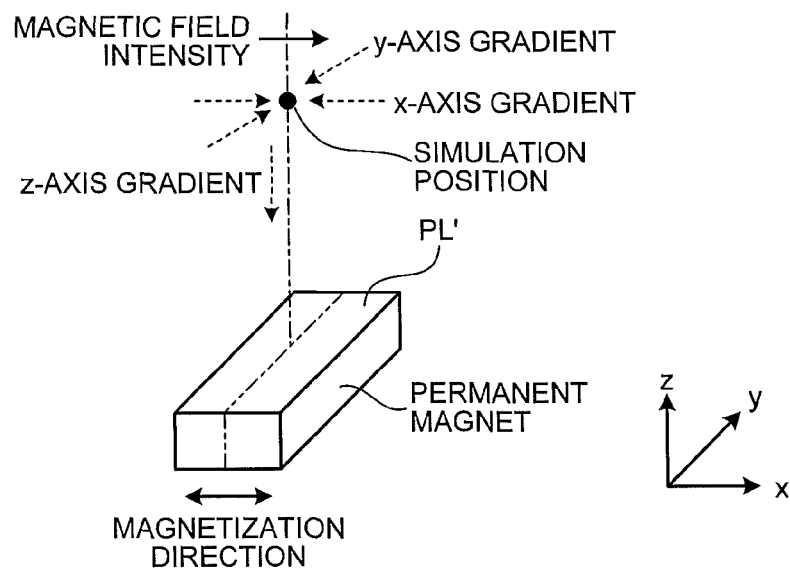
FIG. 15 is a schematic diagram illustrating evaluation items in a simulation for calculating the relationship between the shape of the external permanent magnet and the generated magnetic field.
FIG. 16 is a table illustrating the ratio of the lengths of the sides of each permanent magnet used in the simulation.

The inventors calculated the relationship between the shape of the permanent magnet (the ratio of length, width, and height) and the generated magnetic field using a simulation in order to effectively generate the magnetic field for guiding the capsule endoscope 10 from the external permanent magnet 25a. FIG. 15 is a schematic diagram illustrating evaluation items in the simulation. As illustrated in FIG. 15, in this simulation, the magnetization direction of the permanent magnet was set to the x-axis direction, a direction perpendicular to the magnetization direction of a plane PL' facing a simulation position was set to the y-axis direction, a direction perpendicular to the plane PL' was set to the z-axis direction, and magnetic field intensity at the simulation position and each magnetic field gradient in the z-axis direction, the x-axis direction, and the y-axis direction at the same position were evaluated. The magnetic field intensity is concerned with the guide of the capsule endoscope 10 when the azimuth and the inclination angle are changed. The magnetic field gradient in the z-axis direction is concerned with the guide of the capsule endoscope 10 in the z-axis direction. The magnetic field gradient in the x-axis direction is concerned with the guide of the capsule endoscope 10 in the x-axis direction. The magnetic field gradient in the y-axis direction is concerned with the guide of the capsule endoscope 10 in the y-axis direction.

In this simulation, a permanent magnet with a rectangular parallelepiped shape (including a cubic shape) was used. FIG. 16 is a table illustrating the ratio of the sides of the permanent magnet used in the simulation. In FIG. 16, a "length in the x-axis direction" corresponds to the length of a side which is parallel to the x-axis, a "length in the y-axis direction" corresponds to the length of a side which is parallel to the y-axis, and a "length in the z-axis direction" corresponds to the length of a side which is parallel to the z-axis. In addition, the sides of each permanent magnet are sequentially written in a field "type" illustrated in FIG. 16 in decreasing order of length from the left. For example, a type "x-y-z" indicates a rectangular parallelepiped shape in which the side parallel to the x-axis is the longest and the side parallel to the z-axis is the shortest. In addition, a type "xyz" indicates a cube in which all sides have the same length.

Figure 17:
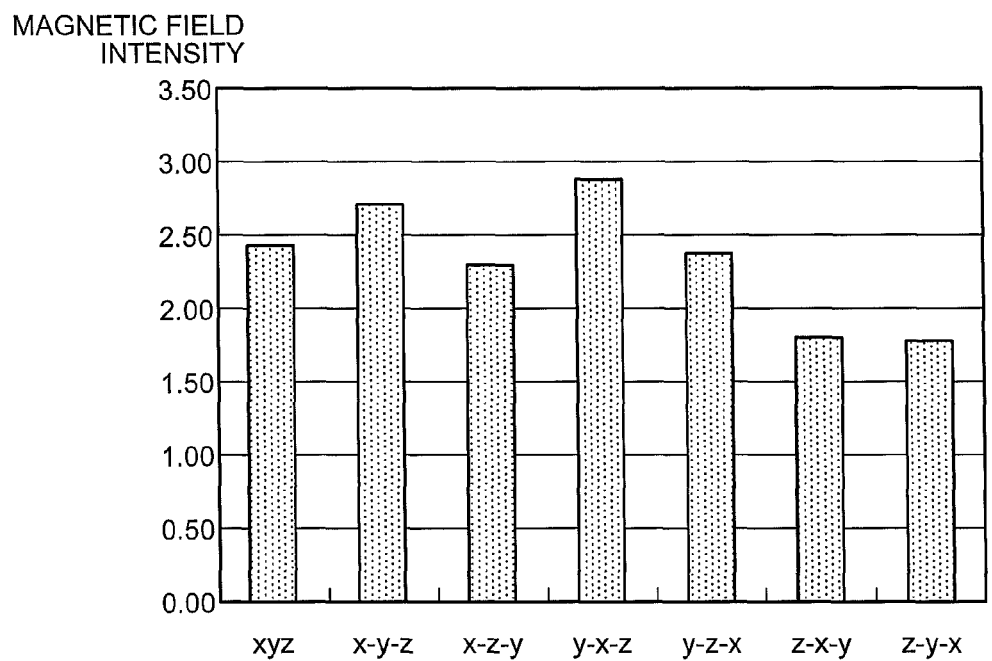
FIG. 17 is a graph illustrating the magnetic field intensity of each permanent magnet illustrated in FIG. 16.
Figure 18:
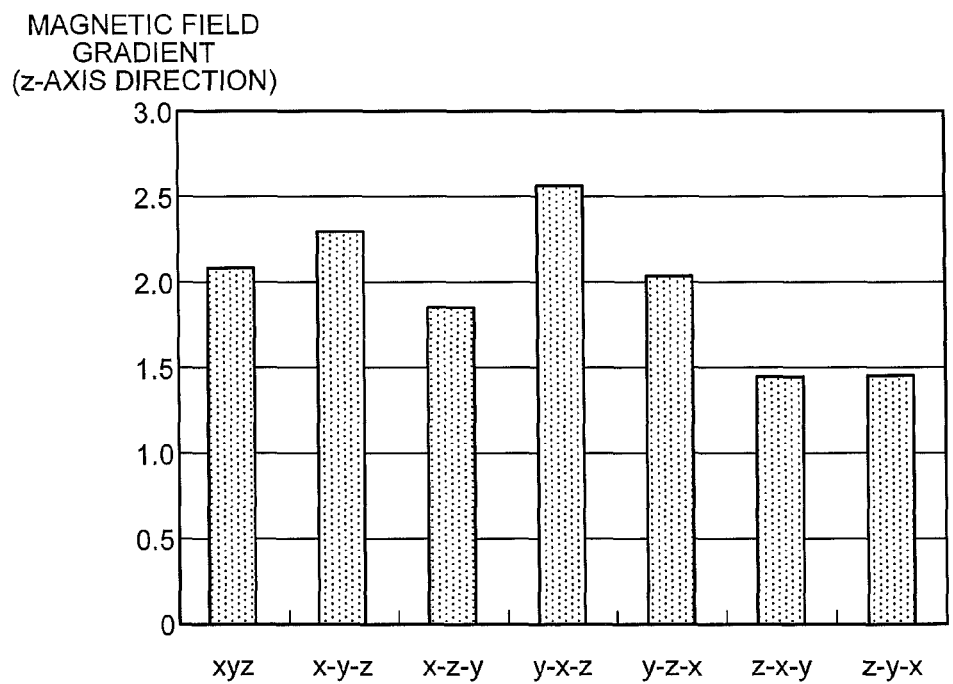
FIG. 18 is a graph illustrating a magnetic field gradient in the z-axis direction which is generated by each permanent magnet illustrated in FIG. 16.
Figure 19:
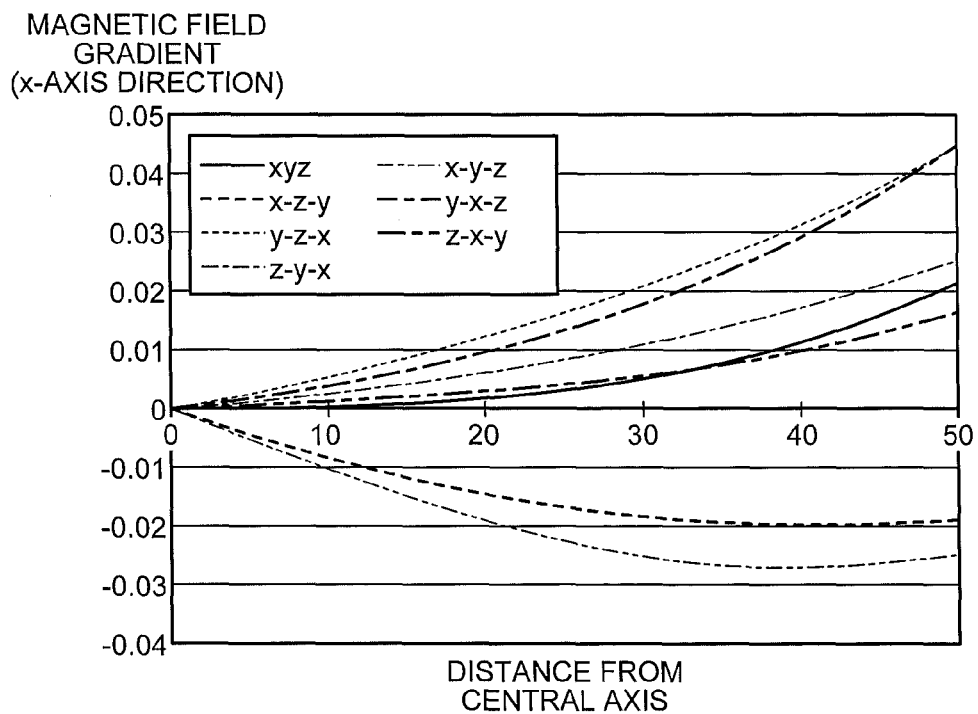
FIG. 19 is a graph illustrating a magnetic field gradient in the x-axis direction which is generated by each permanent magnet illustrated in FIG. 16.
Figure 20:
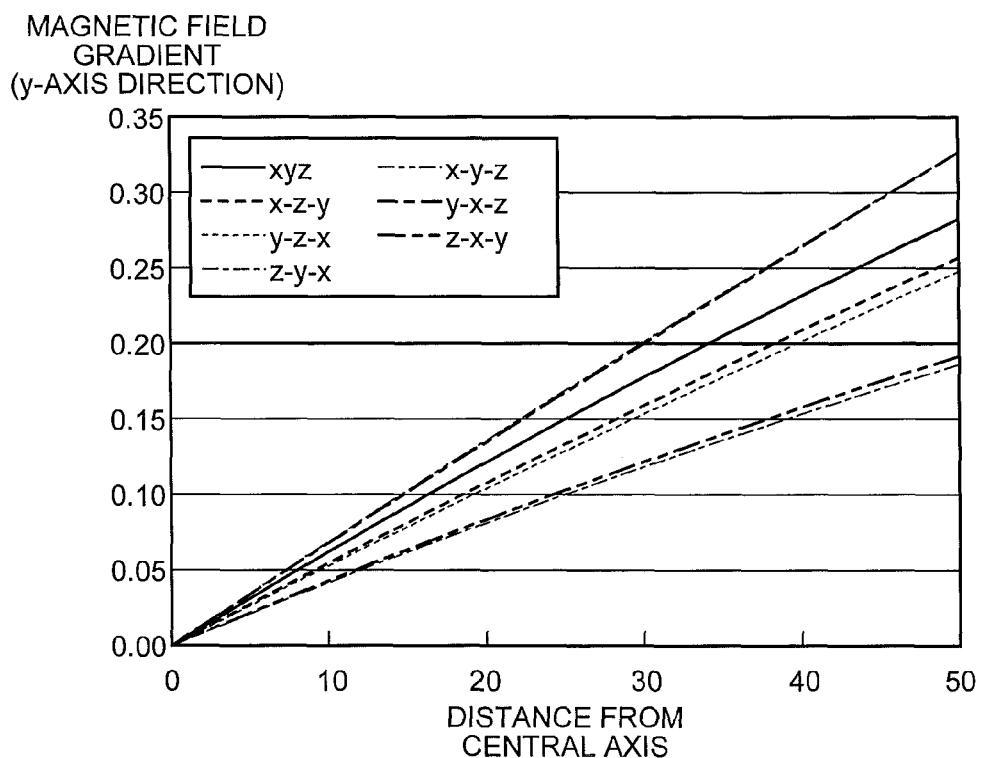
FIG. 20 is a graph illustrating a magnetic field gradient in the y-axis direction which is generated by each permanent magnet illustrated in FIG. 16.

FIG. 17 is a graph illustrating the magnetic field intensity of each permanent magnet illustrated in FIG. 16. FIG. 18 is a graph illustrating the magnetic field gradient in the z-axis direction which is generated by each permanent magnet illustrated in FIG. 16. FIG. 19 is a graph illustrating the magnetic field gradient in the x-axis direction is generated by each permanent magnet illustrated in FIG. 16. FIG. 20 is a graph illustrating the magnetic field gradient in the y-axis direction is generated by each permanent magnet illustrated in FIG. 16. In FIG. 17, the value of the magnetic field intensity is normalized. The value of the magnetic field gradient is normalized through FIGS. 18 to 20. In FIGS. 19 and 20, the horizontal axis indicates a normalized value of the distance from an axis (center axis) in the z-axis direction which passes through the center of the permanent magnet.

It is preferable that the magnetic field intensity generated by the permanent magnet be high in order to effectively control the azimuth and inclination angle of the capsule endoscope 10. In this regard, as illustrated in FIG. 17, relatively high magnetic field intensity was obtained from the magnets of types y-x-z and x-y-z. Therefore, the inventors found that the shape in which the length in the z-axis direction was less than that in the y-axis direction was suitable to control the azimuth and inclination angle of the capsule endoscope 10. In addition, a flat shape in which the length in the z-axis direction is less than that in the x-axis direction and the y-axis direction is more preferable.

When the permanent magnet is rotated in an axis parallel to the y-axis, it is preferable that the permanent magnet have a small projection area when it is projected to the zx plane perpendicular to the y-axis. In this case, it is possible to reduce the moving area of the permanent magnet during rotation. Therefore, it is preferable to reduce the length in the x-axis direction. In this case, the permanent magnet can be provided close to the subject. Therefore, it is possible to generate high-intensity magnetic field in the subject with high efficiency and reduce the size of the guiding magnetic field generation unit 25.

It is preferable that the magnetic field gradient in the vertical direction be large in order to control the position of the capsule endoscope 10 in the vertical direction. In this regard, as illustrated in FIG. 18, a relatively large magnetic field gradient was obtained in the z-axis direction from the magnets of the types y-x-z and x-y-z. Therefore, the inventors found that the shape in which the length in the z-axis direction was small was suitable to control the position of the capsule endoscope 10 in the vertical direction.

It is preferable that the magnetic field gradient in the horizontal direction be large in order to control the position of the capsule endoscope 10 in the horizontal direction. In this regard, as illustrated in FIG. 19, a relatively large magnetic field gradient was obtained in the x-axis direction from the magnets of types y-x-z and y-z-x. In the case of types x-z-y and x-y-z, it was found that the peak of the magnetic field gradient was formed at the position that was away from the permanent magnet. As illustrated in FIG. 20, a relatively large magnetic field gradient was obtained in the y-axis direction from the magnets of types y-x-z and x-y-z. This proves that the shape in which the length in the y-axis direction is more than that in the x-axis direction and the z-axis direction is suitable to control the position of the capsule endoscope 10 in the horizontal direction. In addition, preferably, the length in the x-axis direction is not significantly more than that in the y-axis direction and the z-axis direction.

The simulation result proved that the shape of the external permanent magnet 25a suitable to control the capsule endoscope 10 was a flat plate shape in which the length in the y-axis direction was the largest and the length in the z-axis direction was the smallest. The inventors performed another simulation for calculating the appropriate ratio of the lengths of the sides of the external permanent magnet 25a.

Figures 21, 22:
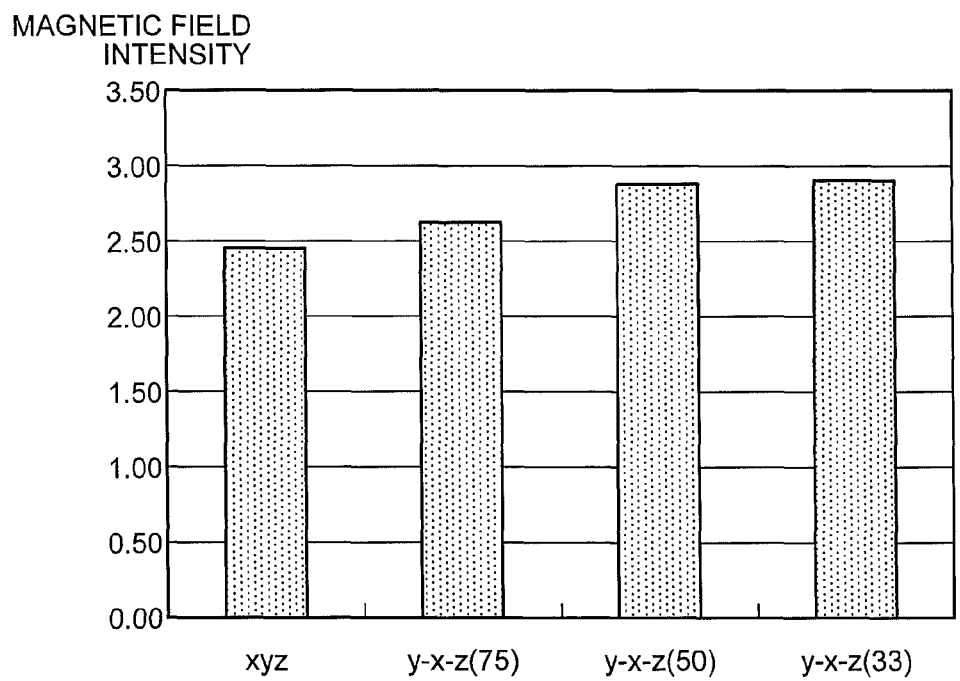
FIG. 21 is a table illustrating the ratio of the lengths of the sides of each permanent magnet used in another simulation.
FIG. 22 is a graph illustrating the magnetic field intensity of each permanent magnet illustrated in FIG. 21.

FIG. 21 is a table illustrating the ratio of the lengths of the sides of each permanent magnet used in another simulation. In FIG. 21, a "length in the x-axis direction" corresponds to the length of a side which is parallel to the x-axis, a "length in the y-axis direction" corresponds to the length of a side which is parallel to the y-axis, and a "length in the z-axis direction" corresponds to the length of a side which is parallel to the z-axis. In FIG. 21, the sides of each permanent magnet are sequentially written in a field "type" in decreasing order of length from the left side and a value in parentheses indicates the ratio of the length in the z-axis direction to the length in the x-axis direction. As illustrated in FIG. 21, in this simulation, all of the permanent magnets have a rectangular parallelepiped shape in which the side parallel to the y-axis direction is the longest and the side parallel to the z-axis direction is the shortest.

Figure 23:
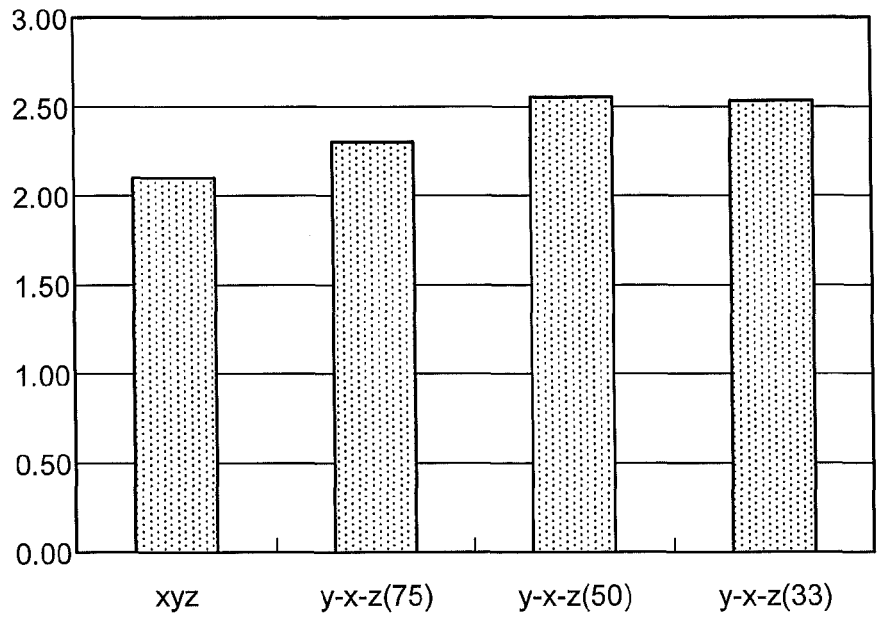
FIG. 23 is a graph illustrating a magnetic field gradient in the z-axis direction which is generated by each permanent magnet illustrated in FIG. 21.
Figure 24:
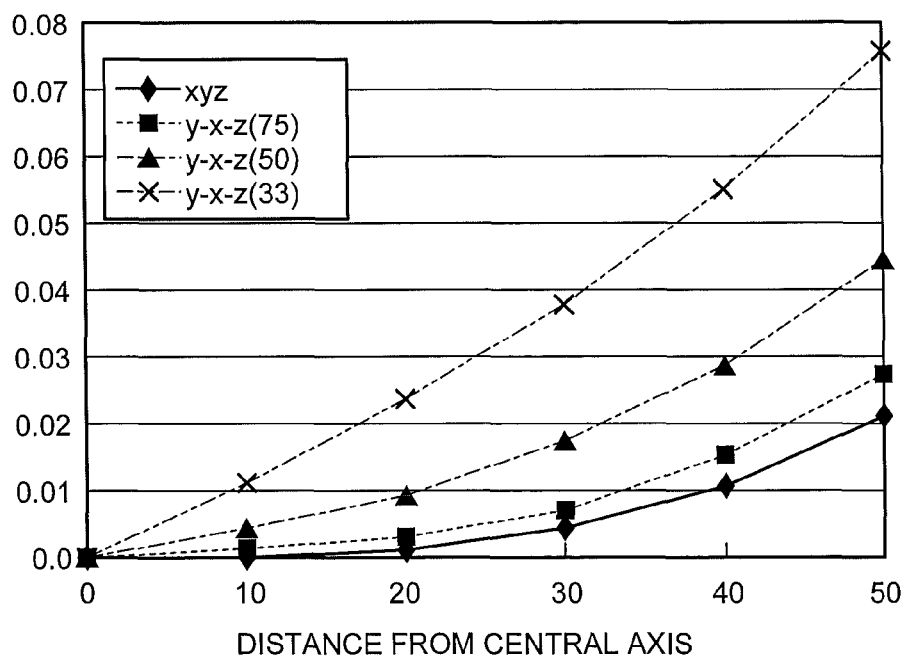
FIG. 24 is a graph illustrating a magnetic field gradient in the x-axis direction which is generated by each permanent magnet illustrated in FIG. 21.
Figure 25:
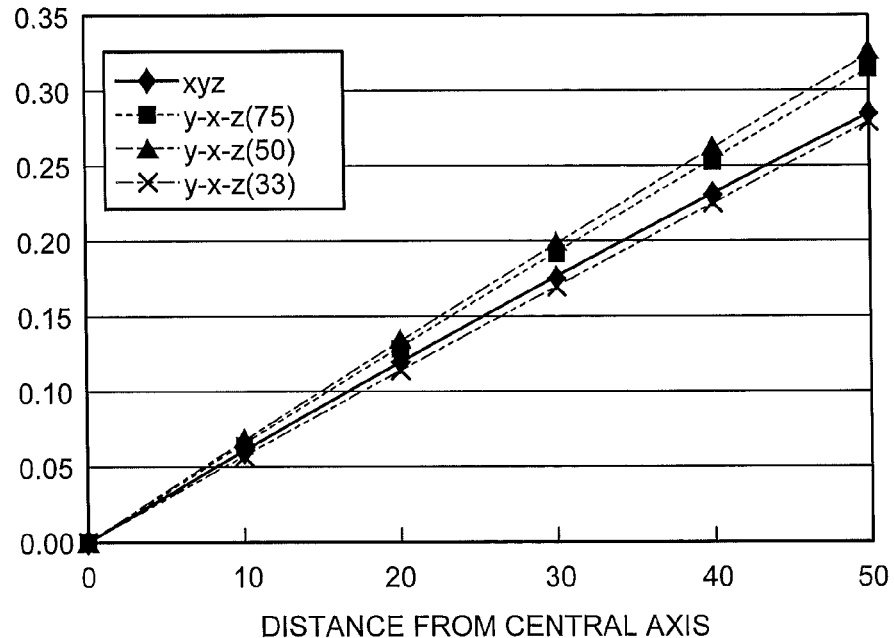
FIG. 25 is a graph illustrating a magnetic field gradient in the y-axis direction which is generated by each permanent magnet illustrated in FIG. 21.

FIG. 22 is a graph illustrating the magnetic field intensity of each permanent magnet illustrated in FIG. 21. FIG. 23 is a graph illustrating a magnetic field gradient in the z-axis direction which is generated by each permanent magnet illustrated in FIG. 21. FIG. 24 is a graph illustrating a magnetic field gradient in the x-axis direction which is generated by each permanent magnet illustrated in FIG. 21. FIG. 25 is a graph illustrating a magnetic field gradient in the y-axis direction which is generated by each permanent magnet illustrated in FIG. 21. In FIG. 22, the value of the magnetic field intensity is normalized. In FIGS. 23 to 25, the value of the magnetic field gradient is normalized. In FIGS. 24 and 25, the horizontal axis indicates a normalized value of the distance from an axis (central axis) in the z-axis direction which passes through the center of the permanent magnet.

As can be seen from FIGS. 22 and 23, for the magnetic field intensity and the magnetic field gradient in the z-axis direction, good results are obtained from all of the permanent magnets and the effect obtained by changing the ratio of the length of each side of the permanent magnet is small.

In contrast, as can be seen from FIG. 24, as the length of the permanent magnet in the y-axis direction increases with respect to the length of the permanent magnet in the z-axis direction (for example, the type y-x-z (33) and the type y-x-z (50)), the magnetic field gradient in the x-axis direction increases significantly. In this case, as can be seen from FIG. 25, when the ratio is too large (for example, the type y-x-z (33)), the magnetic field gradient in the y-axis direction is reduced. However, since the value of the magnetic field gradient in the x-axis direction with respect to the magnetic field gradient in the y-axis direction is small, the ratio of the length in the y-axis direction and the length in the z-axis direction may be determined, considering the balance between the magnetic field gradients in each axis direction.

Figure 26:
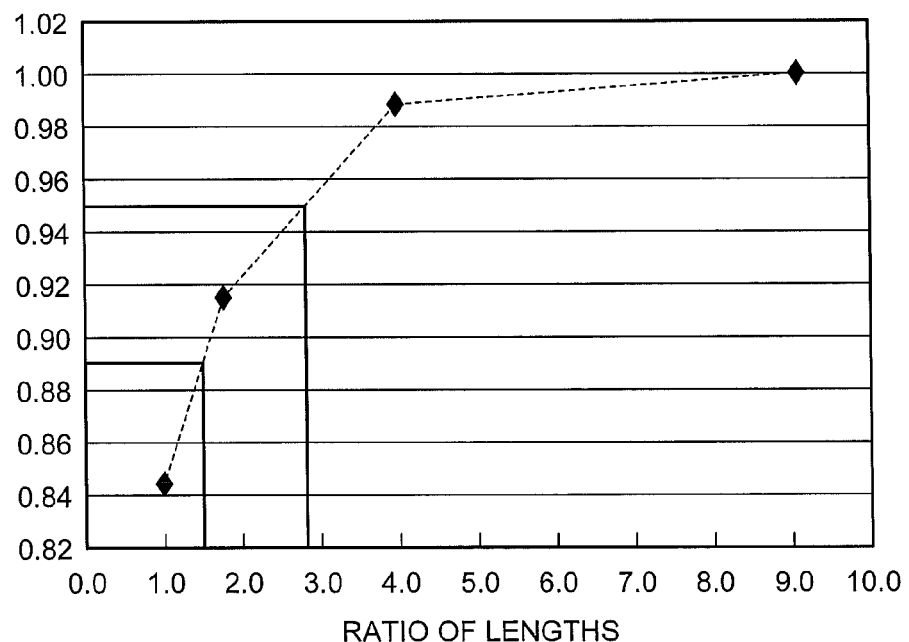
FIG. 26 is a graph illustrating the relationship between the ratio of a length in the y-axis direction to a length in the z-axis direction and the ratio of the magnetic field intensity of the permanent magnets with each dimensional ratio to the magnetic field intensity of a permanent magnet of a type y-x-z (33)

FIG. 26 is a graph illustrating the relationship between the ratio (length ratio) of the length in the y-axis direction to the length in the z-axis direction and the ratio of the magnetic field intensity of the permanent magnets having each of the above-mentioned ratios to the magnetic field intensity of the permanent magnet of the type y-x-z (33). As illustrated in FIG. 26, when the length in the y-axis direction is 1.5 times more than the length in the z-axis direction, it is possible to generate about 90% of the magnetic field intensity of the permanent magnet of the type y-x-z (33), that is, the permanent magnet in which the length in the y-axis direction is sufficiently more than the length in the z-axis direction. When the length in the y-axis direction is equal to or more than three times the length in the z-axis direction, the ratio of the magnetic field intensities is 95%. Therefore, it is preferable that the permanent magnet have a shape in which the length in the y-axis direction is equal to or more than 1.5 times or three times the length in the z-axis direction.

As described above, according to the first embodiment, since a change in the restraint position of the capsule endoscope 10 caused by the rotation of the external permanent magnet 25a is corrected by the translation of the external permanent magnet 25a under the control of the control unit 26, it is possible to improve the operability of the capsule medical device magnetic guiding system by the user.

In addition, according to the first embodiment, the capsule endoscope 10 is guided while floating the liquid introduced into the subject. Therefore, the guiding magnetic field generation unit 25 for guiding the capsule endoscope 10 can be arranged below the bed 20a on which the subject is placed and it is possible to reduce the overall size of the guiding apparatus 20.

In the above-described the first embodiment, a pantoscopic capsule in which the imaging units 11A and 11B are provided at both ends of the capsule endoscope 10 is used. However, a monocular capsule in which the imaging unit is provided at one end of the capsule endoscope may be used. In this case, the position of the center of gravity G of the capsule endoscope is close to the end where the imaging unit is provided, which makes it possible to achieve a capsule endoscope which captures an image only below the surface of water (in water). In addition, the center of gravity G of the capsule endoscope is close to the end where the imaging unit is not provided, which makes it possible to achieve a capsule endoscope which capture the image of a space above the surface of water.

In the above-described the first embodiment, the permanent magnet 19 is arranged such that the magnetization direction is perpendicular to the long axis La of the capsule endoscope 10. However, the permanent magnet 19 may be arranged such that the magnetization direction is aligned with the direction of the long axis La. In this case, the center of gravity G may be provided at a position that deviates from the geometric center C of the capsule endoscope 10 in the diametrical direction. In this case, it is possible to uniquely control the posture of the capsule endoscope 10 in the liquid W.

In the above-described the first embodiment, the center of gravity G is set on the long axis La such that the capsule endoscope 10 floats with the long axis La being aligned with the vertical direction when no magnetic field is applied. However, the position of the center of gravity G may deviate from the long axis La such that the capsule endoscope 10 floats with the long axis La being inclined with respect to the vertical direction when no magnetic field is applied. In this case, it is possible to uniquely control the azimuth and inclination angle of the capsule endoscope 10 in the liquid W.

Alternatively, the center of gravity G of the capsule endoscope may be set so as to deviate from the geometric center C in a direction different from the magnetization direction of the permanent magnet 19. In this case, it is also possible to uniquely control the azimuth and inclination angle of the capsule endoscope 10 in the liquid W.

An electromagnet which generates the same magnetic field as the external permanent magnet 25a may be used as the magnet which generates the magnetic field for guiding the capsule endoscope 10 in the guiding apparatus 20.

In the above-described the first embodiment, the external permanent magnet 25a has a rectangular parallelepiped shape. However, the external permanent magnet 25a may have any shape other than the rectangular parallelepiped as long as a length in the horizontal direction perpendicular to the magnetization direction of the external permanent magnet 25a is more than a length in the magnetization direction and a length in a direction which is perpendicular to the magnetization direction and the horizontal direction perpendicular to the magnetization direction. Preferably, the external permanent magnet 25a may have a shape in which the length in the direction which is perpendicular to the magnetization direction and the horizontal direction perpendicular to the magnetization direction among the lengths in the three directions is the smallest. In this case, it is possible to generate strong magnetic field. In addition, when a permanent magnet with a disk shape or an elliptical disk shape is used, the lengths in the magnetization direction and the first and second directions may be defined by a diameter or the length of the long axis or the short axis.

Modification 1-1

Next, Modification 1-1 of the first embodiment will be described.

In the first embodiment, the control unit 26 calculates the correction direction and the correction amount required to correct a change in the restraint position of the capsule endoscope 10 caused by the rotation of the external permanent magnet 25a, in accordance with the vertical position of the capsule endoscope 10 detected by the position detection unit 22 and the turning angle $\psi$ and elevation angle $\theta$ of the external permanent magnet 25a based on the guide instruction information, or extracts the correction direction and the correction amount from the values which are stored in the storage unit 27 in advance. However, the control unit 26 may acquire the correction direction and the correction amount in accordance with only the guide instruction information. In this case, the correction direction and the correction amount corresponding to the turning angle $\psi$ and elevation angle $\theta$ of the external permanent magnet 25a are stored in the storage unit 27 in advance. Representative values (for example, the average value or maximum value of the correction amount corresponding to each vertical position of the capsule endoscope 10) which are calculated for each angle $\psi$ and each elevation angle $\theta$ in advance may be used as the correction direction and the correction amount stored in the storage unit 27.

When guide instruction information is input from the operation input unit 24, the control unit 26 calculates the turning angle $\psi$, elevation angle $\theta$, translation direction, and translation amount of the external permanent magnet 25a in accordance with the guide instruction information. Then, the control unit 26 extracts the correction direction and the correction amount from the storage unit 27 in accordance with the calculated turning angle $\psi$ and elevation angle $\theta$ and corrects the translation direction and the translation amount based on the guide instruction information using the extracted correction direction and correction amount. In addition, the control unit 26 controls each unit of the guiding magnetic field generation unit 25 such that the external permanent magnet 25a is rotated at the turning angle $\psi$ and the elevation angle $\theta$ based on the guide instruction information and is translated in the corrected translation direction by the corrected translation amount.

According to Modification 1-1, the correction direction and the correction amount are acquired, without using the detection result of the position detection unit 22. Therefore, it is possible to control the guiding magnetic field generation unit 25 at a high speed.

Modification 1-2

Next, Modification 1-2 of the first embodiment will be described.

Modification 1-2 is characterized in that the user manually sets the vertical position H of the capsule endoscope 10 used to calculate the correction amount in stages. For example, the display unit 23 displays a plurality of choices indicating the vertical position H of the capsule endoscope 10 on the screen under the control of the control unit 26. The operation input unit 24 receives a selection signal for selecting one of the plurality of choices from the user and inputs the selection signal to the control unit 26. The control unit 26 sets the vertical position H corresponding to the input selection signal as the current vertical position of the capsule endoscope 10.

The storage unit 27 stores the correction direction and the correction amount corresponding to the turning angle $\psi$, vertical position H, and elevation angle $\theta$ of the internal permanent magnet 25a.

When guide instruction information is input from the operation input unit 24, the control unit 26 acquires the turning angle $\psi$, the elevation angle $\theta$, the translation direction, and the translation amount for controlling the external permanent magnet 25a in accordance with the guide instruction information. Then, the control unit 26 extracts the correction direction and the correction amount from the storage unit 27 in accordance with the acquired turning angle $\psi$ and elevation angle $\theta$ and the currently set vertical position H of the capsule endoscope 10. In addition, the control unit 26 corrects the translation direction and the translation amount based on the guide instruction information, using the extracted correction direction and correction amount, and controls each unit of the guiding magnetic field generation unit 25 such that the external permanent magnet 25a is rotated at the turning angle $\psi$ and the elevation angle $\theta$ and is translated in the corrected correction direction by the corrected correction amount.

According to Modification 1-2, the correction direction and the correction amount are acquired using the vertical position of the capsule endoscope 10 which is set in stages. Therefore, it is possible to control the guiding magnetic field generation unit 25 at a high speed and improve the accuracy of correction.

Modification 1-3

Next, Modification 1-3 of the first embodiment will be described.

In Modification 1-3, the guiding apparatus 20 may include at least two guide modes which guide the capsule endoscope 10 and can be selected by the user. In this case, for example, the display unit 23 displays a plurality of choices indicating the guide modes of the capsule endoscope 10 on the screen under the control of the control unit 26.

For example, the following guide modes (a) to (c) can be selected by the user:

(a) A mode which attracts the capsule endoscope 10 downward in the vertical direction and guides the capsule endoscope 10, with the capsule endoscope 10 coming into contact with, for example, the intestinal wall;

(b) A mode which attracts the capsule endoscope 10 upward in the vertical direction and guides the capsule endoscope 10, with the capsule endoscope 10 coming into contact with, for example, the intestinal wall or the surface of the liquid; and (c) A mode in which the capsule endoscope 10 floats in the liquid, without coming into contact with the intestinal wall or the surface of the liquid.

The operation input unit 24 receives a selection signal for selecting one of a plurality of choices from the user and inputs the selection signal to the control unit 26. The control unit 26 sets a guide mode corresponding to the input selection signal as the current guide mode and controls the guiding magnetic field generation unit 25 such that the capsule endoscope 10 is guided in the set guide mode.

When guide instruction information is input from the operation input unit 24, the control unit 26 calculates the turning angle $\psi$, the elevation angle $\theta$, the translation direction, and the translation amount for controlling the external permanent magnet 25a and acquires the correction direction and the correction amount in accordance with the calculated turning angle $\psi$ and elevation angle $\theta$ and the current guide mode (see the first embodiment and Modifications 1-1 to 1-3). The reason is that the height of the capsule endoscope 10, that is, the distance from the external permanent magnet 25a in the height direction is different in a state (corresponding to (a)) in which the capsule endoscope 10 is disposed in the vicinity of the bottom of the liquid, in a state (corresponding to (b)) in which the capsule endoscope 10 is disposed in the vicinity of the surface of the liquid, and in a state (corresponding to (c)) in which the capsule endoscope 10 floats in the liquid and the translation direction or translation amount of the capsule endoscope 10 is changed due to the rotation of the external permanent magnet 25a. The control unit 26 acquires the correction direction and the correction amount in consideration of the state of the capsule endoscope 10, or adjusts the acquired correction direction and correction amount in consideration of the state of the capsule endoscope 10.

Modification 1-4

Next, Modification 1-4 of the first embodiment will be described.

In Modification 1-4, the control unit 26 acquires information about the azimuth, inclination angle (the inclination of the long axis La), and target position (coordinates in the X-axis, Y-axis, and Z-axis directions) of the capsule endoscope 10 that are desired by the user, in accordance with the guide instruction information input from the operation input unit 24. Then, the control unit 26 rotates the external permanent magnet 25a (changes the turning angle ψ and the elevation angle θ) to change the field of view of the capsule endoscope 10 and performs feedback control in accordance with the detection result of the position which is output from the position detection unit 22 at any time such that the position of the capsule endoscope 10 is aligned with a target position.

Modification 1-5

Next, Modification 1-5 of the first embodiment will be described.

Figure 27A:
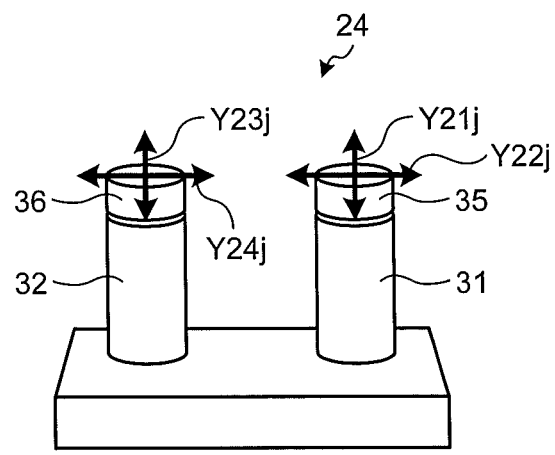
FIGS. 27A and 27B are diagrams illustrating an example of an operation input unit according to Modification 1-5.
Figure 27B:
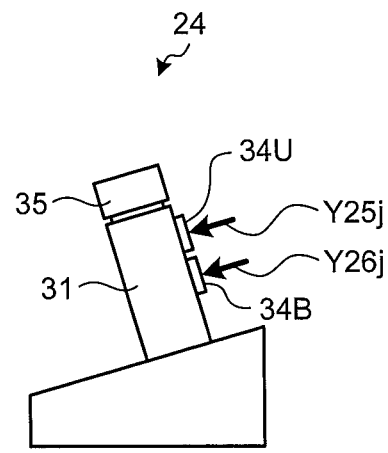
Figure 28:
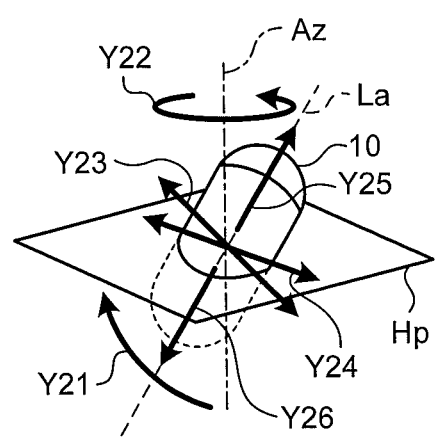
FIG. 28 is a diagram illustrating the magnetic guide of the capsule medical device which can be operated by the operation input unit illustrated in FIG. 27A and FIG. 27B.

FIG. 27A is a front view illustrating an operation input unit 24 according to Modification 1-5, FIG. 27B is a right side view illustrating the operation input unit 24, and FIG. 28 is a diagram illustrating another example of the operation concept of the capsule endoscope 10 instructed by the operation of each component of the operation input unit 24.

Each operation of the operation input unit 24 may be associated with the guide operation of the capsule endoscope 10 such that the capsule endoscope 10 is not guided along the horizontal plane Hp, but can be guided along a plane perpendicular to the long axis La of the capsule endoscope 10, which will be described below. Next, the movement of the capsule endoscope 10 corresponding to the guide operation when the capsule endoscope 10 is guided along the plane perpendicular to the long axis La of the capsule endoscope 10 will be described.

The tilt direction of the joystick 32 with respect to the up-down direction indicated by an arrow Y23j as illustrated in FIG. 27A indicates a down guide direction or an up guide direction in which the capsule endoscope 10 is moved along an arrow Y23 in the plane perpendicular to the long axis La as illustrated in FIG. 28. When operation information corresponding to the tilt operation of the joystick 32 along the arrow Y23j is input from the operation input unit 24 to the control unit 26, the control unit 26 calculates the guide direction and amount of guide of the leading end of the capsule endoscope 10 in the absolute coordinate system according to the tilt direction of the joystick 32, in accordance with the operation information, and controls the first plane position change unit 25b and the vertical position change unit 25c such that the external permanent magnet 25a is translated in accordance with the calculated guide direction and amount of guide.

The tilt direction of the joystick 32 with respect to the left-right direction indicated by an arrow Y24j as illustrated in FIG. 27A indicates a right guide direction or a left guide direction in which the capsule endoscope 10 is moved along an arrow Y24 in the plane perpendicular to the long axis La as illustrated in FIG. 28. When operation information corresponding to the tilt operation of the joystick 32 along the arrow Y24j is input from the operation input unit 24 to the control unit 26, the control unit 26 calculates the guide direction and amount of guide of the leading end of the capsule endoscope 10 in the absolute coordinate system according to the tilt direction of the joystick 32, in accordance with the operation information, and controls the first plane position change unit 25b such that the external permanent magnet 25a is translated in accordance with the calculated guide direction and amount of guide.

When the up button 34U or the down button 34B is pressed along arrows Y25j and Y26j as illustrated in FIG. 27B, a forward guide direction or a backward guide direction in which the capsule endoscope 10 is moved forward and backward related to the imaging elements 15A and 15B along the long axis La as represented by arrows Y25 and Y26, as illustrated in FIG. 28. When operation information corresponding to the press operation of the up button 34U or the down button 34B along the arrows Y25j and Y26j is input from the operation input unit 24 to the control unit 26, the control unit 26 calculates the guide direction and amount of guide of the leading end of the capsule endoscope 10 in the absolute coordinate system according to the pressed button, in accordance with the operation information, and controls the first plane position change unit 25b and the vertical position change unit 25c such that the external permanent magnet 25a is translated in accordance with the calculated guide direction and amount of calculation.

The tilt direction of the joystick 31 with respect to the up-down direction indicated by an arrow Y21j as illustrated in FIG. 27A corresponds to a tilting guide direction in which the leading end of the capsule endoscope 10 is shaken so as to pass through a vertical axis Az, as represented by an arrow Y21 in FIG. 28. The tilt direction of the joystick 31 with respect to the left-right direction indicated by an arrow Y22j corresponds to a rotation guide direction in which the capsule endoscope 10 is rotated about the vertical axis Az as represented by an arrow Y22 of FIG. 28.

Modification 1-6

Next, Modification 1-6 of the first embodiment will be described.

The position of the capsule endoscope 10 in the subject may be detected by various methods besides the method described in the first embodiment based on the intensity of the radio signal received from the capsule endoscope 10.

For example, the position of the capsule endoscope 10 may be detected in accordance with acceleration applied to the capsule endoscope 10. In this case, an acceleration sensor which three-dimensionally detects the acceleration applied to the capsule endoscope 10 is provided in the capsule endoscope 10 and a radio signal having the detection result of the acceleration sensor superimposed thereon is frequently transmitted. The guiding apparatus 20 adds the acceleration applied to the capsule endoscope 10 in accordance with the detection result of the acceleration sensor superimposed on the received radio signal to calculate the relative amount of change in the position of the capsule endoscope 10 and calculates the current position of the capsule endoscope 10 from the amount of change.

Modification 1-7

Next, Modification 1-7 of the first embodiment will be described.

A method of detecting the AC magnetic field may be used as a method of detecting the position of the capsule endoscope 10 in the subject. In this case, an AC magnetic field generation unit which generates the AC magnetic field is provided in the capsule endoscope 10. A plurality of magnetic field sensors which detect the AC magnetic field are provided in the guiding apparatus 20.

The guiding apparatus 20 can detect the AC magnetic field generated by the capsule endoscope 10 using the plurality of magnetic field sensors which are provided at a plurality of positions and continuously calculate the position and/or direction of the capsule endoscope 10 in accordance with the detection result.

Modification 1-8

Next, Modification 1-8 of the first embodiment will be described.

Another method of detecting the AC magnetic field will be described as the method of detecting the position of the capsule endoscope 10 in the subject. In this case, an LC circuit which is resonated by the AC magnetic field is provided in the capsule endoscope 10. A plurality of magnetic field sensors which detect the AC magnetic field are provided in the guiding apparatus 20.

The guiding apparatus 20 detects in advance a first resonance magnetic field which is generated by the LC circuit in the capsule endoscope 10 when the capsule endoscope 10 is not disposed in a measurement region (a region of the magnetic field generated by the guiding magnetic field generation unit 25) of the subject. Then, the guiding apparatus 20 detects a second resonance magnetic field which is generated by the LC circuit in the capsule endoscope 10 when the capsule endoscope 10 is disposed in the measurement region of the subject and continuously calculates a difference value between the detection value of the first resonance magnetic field and the detection value of the second resonance magnetic field. In addition, the guiding apparatus 20 continuously calculates the position coordinates of the capsule endoscope 10 in the three-dimensional space in accordance with the difference value.

Second Embodiment

Next, a second embodiment of the invention will be described.

Figure 29:
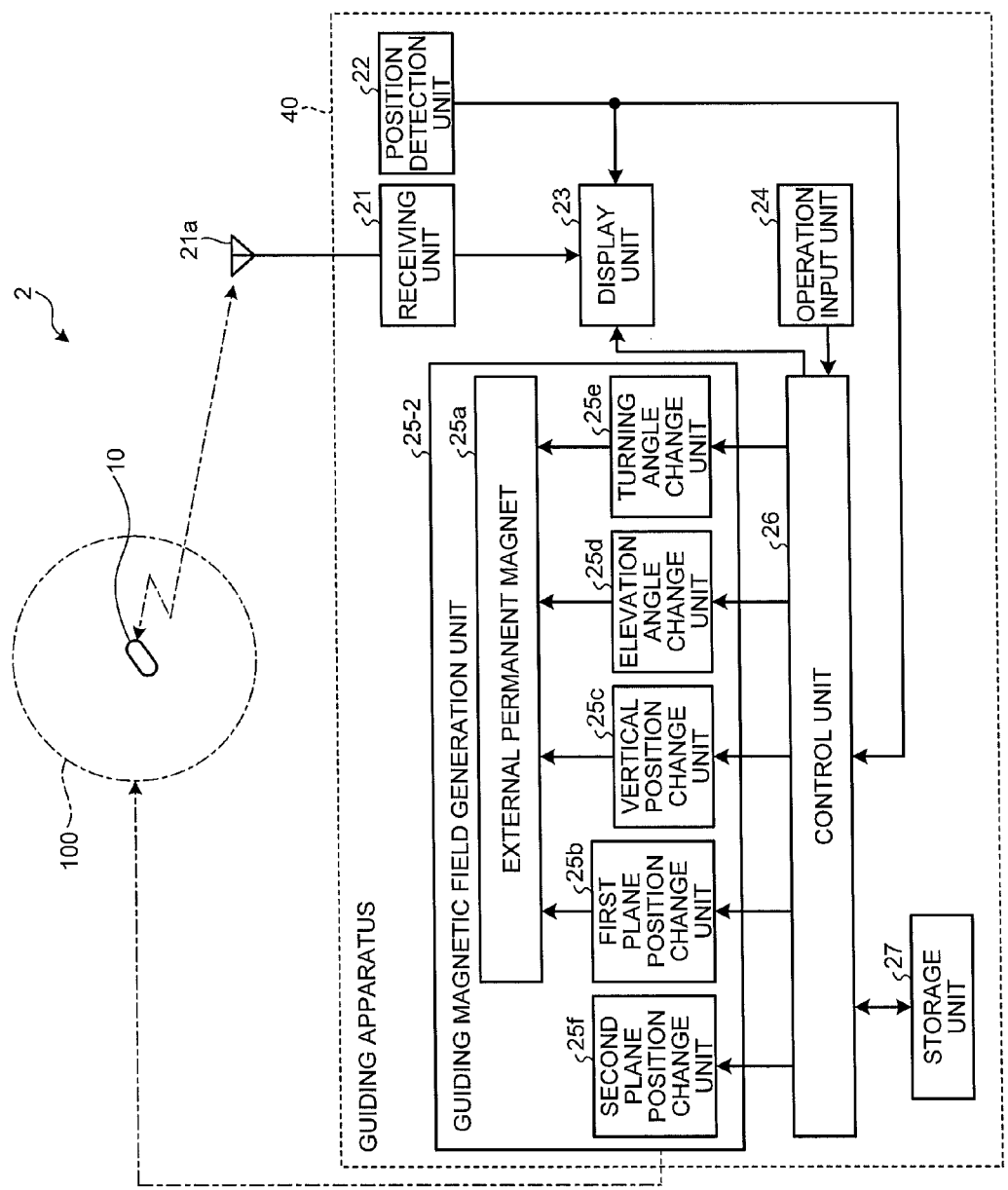
FIG. 29 is a diagram illustrating an example of the structure of a capsule medical device magnetic guiding system according to a second embodiment of the invention.

FIG. 29 is a diagram illustrating an example of the structure of a capsule medical device magnetic guiding system according to the second embodiment. As illustrated in FIG. 29, a capsule medical device magnetic guiding system 2 according to the second embodiment includes a guiding apparatus 40 including a guiding magnetic field generation unit 25-2, instead of the guiding apparatus 20 illustrated in FIG. 1. The guiding magnetic field generation unit 25-2 further includes a second plane position change unit 25f, as compared with the guiding magnetic field generation unit 25 illustrated in FIG. 1. The capsule medical device magnetic guiding system 2 has the same structure as that in the first embodiment except for the second plane position change unit 25f.

Figure 30:
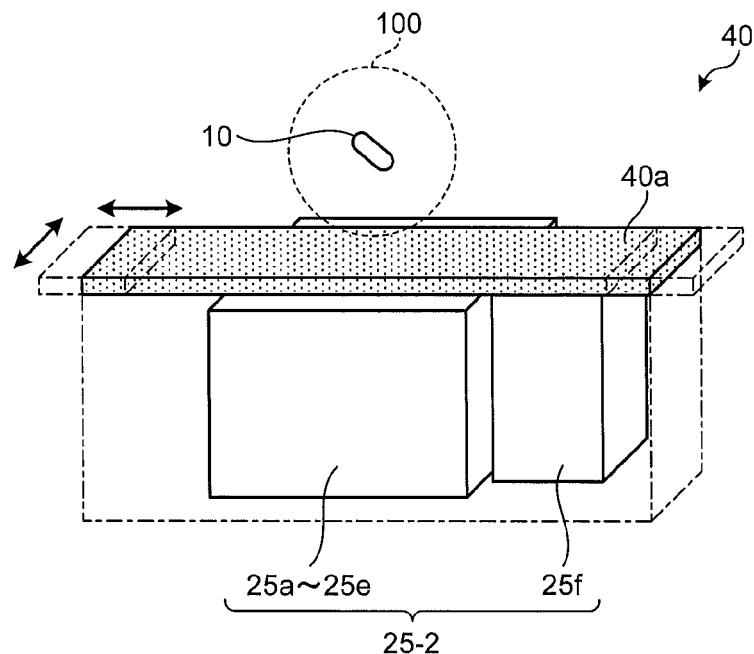
FIG. 30 is a perspective view schematically illustrating the outward appearance of a guiding apparatus illustrated in FIG. 29.

FIG. 30 is a perspective view schematically illustrating the outward appearance of the guiding apparatus 40. As illustrated in FIG. 30, the guiding apparatus 40 includes a bed 40a which can be translated in the horizontal direction as a table on which the subject is placed. The guiding magnetic field generation unit 25-2 which generates a magnetic field 100 is arranged below the bed 40a.

The second plane position change unit 25f is a translation mechanism which translates the bed 40a in the horizontal direction. The second plane position change unit 25f moves the bed 40a on which the subject is placed to change the position of the subject relative to the capsule endoscope 10 which is restrained by the magnetic field 100 generated by the external permanent magnet 25a, that is, the position of the capsule endoscope 10 relative to the subject.

When guide instruction information for translating the capsule endoscope 10 is input from the operation input unit 24, the control unit 26 translates the bed 40a using the second plane position change unit 25f to change the position of the capsule endoscope 10 relative to the subject, in accordance with the input guide instruction information.

When guide instruction information for changing the posture of the capsule endoscope 10 is input from the operation input unit 24, the control unit 26 calculates the turning angle $\psi$ and elevation angle $\theta$ of the external permanent magnet 25a in accordance with the input guide instruction information and calculates a correction direction and a correction amount for correcting a change in the restraint position of the capsule endoscope 10 caused by the rotation of the external permanent magnet 25a. Then, the control unit 26 directs the first plane position change unit 25b to translate the external permanent magnet 25a in accordance with the calculated correction direction and correction amount.

It is difficult for the user to check a change in the restraint position of the capsule endoscope 10 caused by a change in the inclination angle of the capsule endoscope 10 or the correction direction and the correction amount for correcting the change in the restraint position. Therefore, the correction operation which cannot be checked by the user is implemented by the translation of the external permanent magnet 25a arranged below the bed 40a and the translational motion of the capsule endoscope 10 by the operation of the user is implemented by the relative movement of the bed 40a. In this case, since the user can predict the movement of the bed 40a, an examination using the capsule endoscope can be made without discomfort. The external permanent magnet 25a can be translated at a high speed, as compared to the bed 40a on which the subject is placed. Therefore, it is possible to improve the guide performance of the capsule endoscope 10.

As described above, according to the second embodiment, the translation of the capsule endoscope 10 in the horizontal direction is implemented by the translation of the external permanent magnet 25a and the translation of the bed 40a. Therefore, it is possible to reduce the translation amount of the external permanent magnet 25a and to prevent an increase in the size of the guiding apparatus 40.

According to the second embodiment, the translation of the capsule endoscope 10 based on the operation of the user is implemented by the translational motion of the bed 40a and the correction of the capsule endoscope 10 which is not recognized by the user is implemented by the translational motion of the external permanent magnet 25a. Therefore, it is possible to improve the operability of the user.

Modification 2-1

Next, Modification 2-1 of the second embodiment will be described.

In the second embodiment, the translational motion for correcting the restraint position of the capsule endoscope 10 and the translational motion of the capsule endoscope 10 based on the guide instruction information are made by the external permanent magnet 25a and the bed 40a, respectively. However, the total translational motion of the capsule endoscope 10 may be distributed to the external permanent magnet 25a and the bed 40a at a predetermined ratio.

That is, when guide instruction information is input from the operation input unit 24, the control unit 26 acquires the turning angle $\psi$, elevation angle $\theta$, translation direction, and translation amount for controlling the external permanent magnet 25a in accordance with the guide instruction information. In addition, similarly to the first embodiment and Modifications 1-1 to 1-3, the control unit 26 acquires a correction direction and a correction amount for correcting a change in the restraint position of the capsule endoscope 10 caused by the rotation of the external permanent magnet 25a. Then, the control unit 26 corrects the translation direction and the translation amount based on the guide instruction information with the acquired correction direction and correction amount. In addition, the control unit 26 divides the corrected translation amount into the translation amount of the external permanent magnet 25a and the translation amount of the bed 40a at a predetermined ratio.

The ratio is not particularly limited. The translation amount may be equally distributed to the external permanent magnet 25a and the bed 40a, priority may be given to the translation by the external permanent magnet 25a, or priority may be given to the translation by the bed 40a. In addition, at that time, the translational velocity of the external permanent magnet 25a and the bed 40a may be adjusted in accordance with the translation amounts of the external permanent magnet 25a and the bed 40a such that the movement of the capsule endoscope 10 is completed within a predetermined period of time.

According to Modification 2-1, it is possible to reduce the translation amounts of the external permanent magnet 25a and the bed 40a. Therefore, it is possible to further prevent an increase in the size of the guiding apparatus 40.

Modification 2-2

Next, Modification 2-2 of the second embodiment will be described.

There is a physical upper limit in the translational velocity of the external permanent magnet 25a and the bed 40a. In particular, since the subject is placed on the bed 40a, it is difficult to move the bed 40a at a high speed. Therefore, when the translation amount (including the corrected translation amount) for translating the capsule endoscope 10 is large and the total translation amount is distributed to the external permanent magnet 25a and the bed 40a at a predetermined ratio, it is considered that the movement of the capsule endoscope 10 is not completed within a predetermined period of time and the position of the capsule endoscope 10 greatly deviates from the intended position. In this case, it is preferable to change the distribution ratio of the total translation amount and optimize the translation amount of the external permanent magnet 25a and the translation amount of the bed 40a.

For example, when the total translation amount is distributed to the external permanent magnet 25a and the bed 40a at a predetermined ratio and the speed or translation amount of one of the external permanent magnet 25a and the bed 40a is more than the upper limit speed or the upper limit translation amount defined by the speed, the translation amount of one of the external permanent magnet 25a and the bed 40a whose speed is not more than the upper limit speed (for example, the bed 40a) is distributed to the other whose speed is not more than the upper limit speed (for example, the external permanent magnet 25a).

In this case, the upper limit speed of the external permanent magnet 25a may be set to be more than that of the bed 40a. The reason is that it is possible to translate the external permanent magnet 25a at a high speed, as compared to the bed 40a on which the subject is placed. This setting makes it possible to increase the translation amount of the external permanent magnet 25a and increase the translational velocity. Therefore, it is possible to improve the guide performance of the capsule endoscope 10.

Third Embodiment

Next, a third embodiment of the invention will be described.

Figure 31:
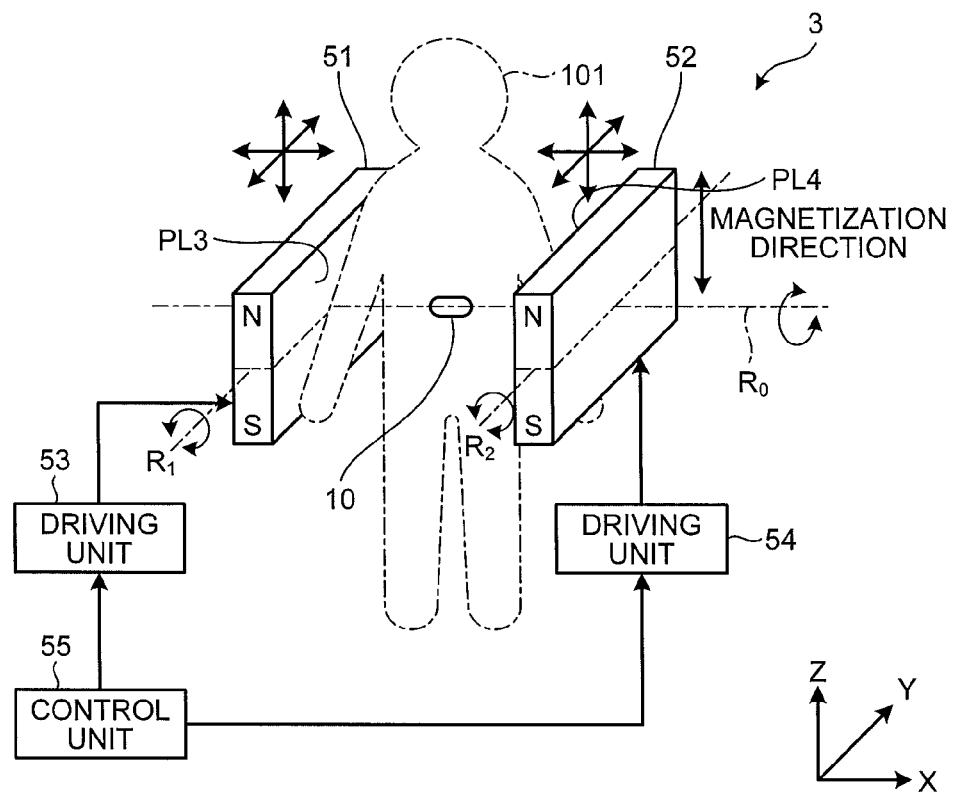
FIG. 31 is a schematic diagram illustrating an example of the structure of a capsule medical device guiding system according to a third embodiment of the invention.

FIG. 31 is a schematic diagram illustrating an example of the structure of a capsule medical device guiding system according to the third embodiment. As illustrated in FIG. 31, a capsule medical device magnetic guiding system 3 according to the third embodiment includes a capsule endoscope 10 which includes a permanent magnet 19 and is introduced into a subject 101, permanent magnets 51 and 52 which are arranged on both sides of the subject 101 so as to be opposite to each other, driving units 53 and 54 which respectively drive the permanent magnets 51 and 52, and a control unit 55 which controls the operation of the driving units 53 and 54. The capsule endoscope 10 is restrained by the magnetic field which is formed in the subject 101 by the permanent magnets 51 and 52 and the position and posture of the capsule endoscope 10 are controlled by the operation of the permanent magnets 51 and 52.

The permanent magnets 51 and 52 are permanent magnets which are the same type and have the same rectangular parallelepiped shape. The permanent magnets 51 and 52 are arranged in parallel to each other such that one plane (hereinafter, referred to as a capsule opposite plane PL3 or PL4) among four planes parallel to their magnetization directions faces the subject 101 and they are mirror-symmetrically arranged. The permanent magnets 51 and 52 are arranged such that their magnetization directions are aligned with the vertical direction (Z-axis direction) in an initial state. Hereinafter, among the directions perpendicular to the vertical direction when the capsule endoscope 10 is not guided, a direction perpendicular to the capsule opposite planes PL3 and PL4 is referred to as the X-axis direction and a direction parallel to the capsule opposite planes PL3 and PL4 is referred to as the Y-axis direction.

The permanent magnets 51 and 52 each have a shape in which, among the lengths of the sides in three directions of the rectangular parallelepiped, the length of a side in the direction (in FIG. 31, the Y-axis direction) in the capsule opposite planes PL3 and PL4 perpendicular to the magnetization direction is more than that in the magnetization direction (in FIG. 31, the Z-axis direction) and a direction (in FIG. 31, the X-axis direction) perpendicular to the capsule opposite planes PL3 and PL4. Preferably, the permanent magnets 51 and 52 each have a flat plate shape in which, among the lengths of the sides in three directions of the rectangular parallelepiped, the length of a side in the direction perpendicular to the capsule opposite planes PL3 and PL4 is the smallest.

The permanent magnets 51 and 52 are configured such that they can be translated in the horizontal direction and the vertical direction. Therefore, it is possible to control the position of the capsule endoscope 10 in the subject 101. For example, the permanent magnets 51 and 52 are translated in the vertical plane to change the position of the capsule endoscope 10 in the vertical plane. In addition, the permanent magnets 51 and 52 are translated in the horizontal plane to change the position of the capsule endoscope 10 in the horizontal plane.

The permanent magnets 51 and 52 are configured so as to be rotatable about an axis $R_0$ which is perpendicular to the capsule opposite planes PL3 and PL4 and passes through the centers of the capsule opposite planes PL3 and PL4 and axes $R_1$ and $R_2$ which are in the capsule opposite planes PL3 and PL4 and are perpendicular to the magnetization direction. Therefore, it is possible to control the azimuth and inclination angle of the capsule endoscope 10 in the subject 101. For example, when the permanent magnets 51 and 52 are rotated (turned) about the axis $R_0$ while maintaining the positional relationship therebetween, the capsule endoscope 10 follows the rotation and the azimuth of the capsule endoscope 10 is changed. When the permanent magnets 51 and 52 are inclined with respect to the axes $R_1$ and $R_2$, respectively, while maintaining the positional relationship therebetween, the capsule endoscope 10 follows the inclination and is inclined.

As described above, according to the first to third embodiments and modifications thereof, when information about the rotation of the capsule medical device is input, the capsule medical device is translated relative to the subject to correct a change in the position of the capsule medical device caused by the rotation of the magnetic field generation unit. Therefore, it is possible to improve the operability of the capsule medical device magnetic guiding system by the user.

The above-described embodiments are limited to examples for implementing the invention and the invention is not limited to the above-described embodiments. In addition, a plurality of components disclosed in the embodiments or modifications of the invention can be appropriately combined with each other to form various structures. In addition, various modifications and changes of the invention can be made according to, for example, specifications and it will be apparent from the above that various other embodiments can be made within the scope of the invention.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

APPENDIX 1

A capsule medical device guiding system including:
a capsule medical device that includes a permanent magnet and is introduced into a subject; and
a guiding apparatus that guides the capsule medical device in the subject by applying a magnetic field to the capsule medical device,
wherein the guiding apparatus includes:
a magnetic field generation unit;
a translation mechanism that translates the magnetic field generation unit relative to the subject;
a rotation mechanism that rotates the magnetic field generation unit relative to the subject;
an input unit that receives first information about an operation for changing a position of the capsule medical device and second information about an operation for changing a posture of the capsule medical device; and
a control unit that controls the translation mechanism and the rotation mechanism in accordance with the first information and the second information such that the magnetic field generation unit is translated and rotated relative to the subject, and
when the input unit receives the second information, the control unit corrects a change in the position of the capsule medical device caused by the rotation of the magnetic field generation unit relative to the subject by translating the magnetic field generation unit relative to the subject.

APPENDIX 2

The capsule medical device guiding system according to Appendix 1,
wherein the permanent magnet of the capsule medical device is arranged such that an angle is formed between a magnetization direction thereof and a long-axis direction of the capsule medical device.

APPENDIX 3

The capsule medical device guiding system according to Appendix 1,
wherein the permanent magnet of the capsule medical device is arranged such that a magnetization direction thereof is parallel to a long-axis direction of the capsule medical device.

APPENDIX 4

The capsule medical device guiding system according to Appendix 2 or 3,
wherein the center of gravity of the capsule medical device is arranged at a position that deviates from a geometric center of the capsule medical device in a direction different from the magnetization direction.

APPENDIX 5

The capsule medical device guiding system according to any one of Appendixes 2 to 4,
wherein the capsule medical device includes at least one imaging element in which a direction of an imaging surface with respect to the magnetization direction is fixed.

APPENDIX 6

The capsule medical device guiding system according to any one of Appendixes 1 to 5,
wherein the capsule medical device includes two imaging units that are provided at both ends thereof in the long-axis direction.

What is claimed is:
1. A guiding apparatus for guiding, in a subject, a capsule medical device introduced into the subject and including a permanent magnet by applying a magnetic field to the capsule medical device, the guiding apparatus comprising:
   a magnetic field generation unit;
   a translation mechanism that translates the magnetic field generation unit relative to the subject;
   a rotation mechanism that rotates the magnetic field generation unit relative to the subject;
   an input unit that receives first information about an operation for changing a position of the capsule medical device and second information about an operation for changing a posture of the capsule medical device; and
   a control unit that controls the translation mechanism and the rotation mechanism in accordance with the first information and the second information such that the magnetic field generation unit is translated and rotated relative to the subject,
   wherein, when the input unit receives the second information, the control unit corrects a change in the position of the capsule medical device caused by the rotation of the magnetic field generation unit relative to the subject by translating the magnetic field generation unit relative to the subject.
2. The guiding apparatus according to claim 1,
   wherein the rotation mechanism includes a mechanism that rotates the magnetic field generation unit relative to the subject in a vertical plane including a magnetization direction of the magnetic field generation unit, and when the mechanism rotates the magnetic field generation unit in accordance with the second information, the control unit corrects the change in the position of the capsule medical device caused by the rotation of the magnetic field generation unit by translating the magnetic field generation unit relative to the subject in a direction which is parallel to an intersection line between the vertical plane and a horizontal plane.

3. The guiding apparatus according to claim 1, wherein the rotation mechanism includes a second mechanism that rotates the magnetic field generation unit about a vertical axis relative to the subject, with the magnetization direction of the magnetic field generation unit being inclined with respect to the vertical axis, and when the second mechanism rotates the magnetic field generation unit in accordance with the second information, the control unit corrects the change in the position of the capsule medical device caused by the rotation of the magnetic field generation unit by translating the magnetic field generation unit in the horizontal plane relative to the subject.

4. The guiding apparatus according to claim 1, further comprising:

a table on which the subject into which the capsule medical device is introduced is placed, wherein the translation mechanism includes a first translation mechanism that translates the magnetic field generation unit and a second translation mechanism that translates the table, and the control unit translates the magnetic field generation unit relative to the subject by the first translation mechanism for a portion of a total translation amount, by which the translation mechanism translates the magnetic field generation unit relative to the subject in accordance with the first information and the second information, and by the second translation mechanism for the remaining translation amount.

5. The guiding apparatus according to claim 4, wherein, when the input unit receives the second information, the control unit corrects the change in the position of the capsule medical device caused by the rotation of the magnetic field generation unit relative to the subject by translating the magnetic field generation unit only by the first translation mechanism.

6. The guiding apparatus according to claim 4, wherein the control unit divides the total translation amount into a translation amount by the first translation mechanism and a translation amount by the second translation mechanism at a predetermined ratio.

7. The guiding apparatus according to claim 4, wherein the control unit divides the total translation amount into a translation amount by the first translation mechanism and a translation amount by the second translation mechanism in accordance with upper limit speeds of the first translation mechanism and the second translation mechanism.

8. The guiding apparatus according to claim 1, further comprising:

a position detection unit that detects the position of the capsule medical device, wherein the control unit calculates, in accordance with a detection result of the position detection unit and a rotation angle of the magnetic field generation unit, a translation amount by which the magnetic field generation unit is translated relative to the subject.

9. The guiding apparatus according to claim 1, further comprising:

a position detection unit that detects the position of the capsule medical device; and a storage unit that stores a relationship of a distance between the capsule medical device and the magnetic field generation unit and a rotation angle of the magnetic field generation unit with a translation amount by which the magnetic field generation unit is translated relative to the subject, wherein the control unit extracts the translation amount from the storage unit in accordance with the distance between the capsule medical device and the magnetic field generation unit which is calculated from a detection result of the position detection unit and the rotation angle of the magnetic field generation unit which is controlled in accordance with the second information received by the input unit.

10. The guiding apparatus according to claim 1, further comprising:

a storage unit that stores a relationship between a rotation angle of the magnetic field generation unit and a representative value of a translation amount by which the magnetic field generation unit is translated relative to the subject, wherein the control unit extracts the translation amount from the storage unit in accordance with the rotation angle of the magnetic field generation unit which is controlled in accordance with the second information received by the input unit.

11. The guiding apparatus according to claim 1, further comprising:

a storage unit that stores a relationship of a distance between the capsule medical device and the magnetic field generation unit and a rotation angle of the magnetic field generation unit with a translation amount by which the magnetic field generation unit is translated relative to the subject, wherein the input unit further receives information about the distance between the capsule medical device and the magnetic field generation unit, and the control unit extracts the translation amount from the storage unit in accordance with the information about the distance which is received from the input unit and the rotation angle of the magnetic field generation unit which is controlled in accordance with the second information.

12. The guiding apparatus according to claim 1, wherein the input unit further receives information about a guide mode of the capsule medical device, the guiding apparatus further comprises a storage unit that stores a relationship of the guide mode and a rotation angle of the magnetic field generation unit with a translation amount by which the magnetic field generation unit is translated relative to the subject, and the control unit extracts the translation amount from the storage unit in accordance with the information about the guide mode which is received by the input unit.

13. The guiding apparatus according to claim 1, further comprising:

a position detection unit that detects the position of the capsule medical device, wherein the control unit acquires target position information of the capsule medical device in accordance with at least the second information received by the input unit and controls the position of the capsule medical device in accordance with the target position information and a detection result of the position detection unit.

14. The guiding apparatus according to claim 1, wherein the magnetic field generation unit is a permanent magnet.

15. A capsule medical device guiding system comprising:
a capsule medical device that includes a permanent magnet; and
a guiding apparatus that applies a magnetic field to the capsule medical device introduced into a subject to guide the capsule medical device in the subject,
wherein the guiding apparatus comprises:
a magnetic field generation unit;
a translation mechanism that translates the magnetic field generation unit relative to the subject;
a rotation mechanism that rotates the magnetic field generation unit relative to the subject;
an input unit that receives first information about an operation for changing a position of the capsule medical device and second information about an operation for changing a posture of the capsule medical device; and
a control unit that controls the translation mechanism and the rotation mechanism in accordance with the first information and the second information such that the magnetic field generation unit is translated and rotated relative to the subject,
wherein, when the input unit receives the second information, the control unit corrects a change in the position of the capsule medical device caused by the rotation of the magnetic field generation unit relative to the subject by translating the magnetic field generation unit relative to the subject.

* * * * *